(12) United States Patent
Baxter, III et al.

(10) Patent No.: US 10,646,254 B2
(45) Date of Patent: May 12, 2020

(54) SHIFTING BURR CAP ASSEMBLY

(71) Applicant: Medtronic, Inc., Minneapolis, MN (US)

(72) Inventors: Walton W. Baxter, III, San Clemente, CA (US); Byron Johnson, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 170 days.

(21) Appl. No.: 15/697,037

(22) Filed: Sep. 6, 2017

(65) Prior Publication Data
US 2019/0069927 A1    Mar. 7, 2019

(51) Int. Cl.
*A61B 17/34* (2006.01)
*A61N 1/05* (2006.01)
(Continued)

(52) U.S. Cl.
CPC ......... *A61B 17/3468* (2013.01); *A61M 25/02* (2013.01); *A61M 39/02* (2013.01); *A61N 1/0529* (2013.01); *A61N 1/0534* (2013.01); *A61N 1/0539* (2013.01); *A61N 1/37247* (2013.01); *A61N 1/37264* (2013.01);
(Continued)

(58) Field of Classification Search
CPC .......... A61B 17/3468; A61B 2090/103; A61B 5/6864; A61M 25/02; A61M 39/02; A61M 2039/025; A61M 2210/0687; A61N 1/0529; A61N 1/0534; A61N 1/0539
See application file for complete search history.

(56) References Cited

U.S. PATENT DOCUMENTS 5,916,200 A * 6/1999 Eppley ................. A61M 25/02
604/174
6,321,104 B1    11/2001 Gielen et al.
(Continued)

FOREIGN PATENT DOCUMENTS

| EP | 1016432 B1 | 5/2005 |
|---|---|---|
| WO | 2006062892 A2 | 6/2006 |
| WO | 2012027791 A1 | 3/2012 |

OTHER PUBLICATIONS

International Search Report and Written Opinion of International Application No. PCTUS2018/037688, dated Aug. 16, 2018, 12 pp.
(Continued)

*Primary Examiner* — Christopher A Flory
(74) *Attorney, Agent, or Firm* — Shumaker & Sieffert, P.A.

(57) ABSTRACT

A burr cap assembly is at least partially inserted into a burr hole within the cranium of a patient. The burr cap assembly enables a elongate member to be inserted through the burr cap assembly to access a brain of the patient. A shifting member of the burr cap assembly may be configured to enable the elongate member to move with shifting fluid and matter of the brain. The shifting member of the burr cap assembly may be configured to move within a cavity defined by the burr cap assembly. The shifting member may be configured to move in a direction that is substantially perpendicular to a longitudinal axis of the distal portion of the elongate member. The shifting member may at least partially retain the elongate member, so as the shifting brain applies forces upon the elongate member, the elongate member and the shifting member may move within the cavity.

25 Claims, 11 Drawing Sheets

(51) Int. Cl.
*A61M 25/02* (2006.01)
*A61M 39/02* (2006.01)
*A61B 90/10* (2016.01)
*A61N 1/372* (2006.01)

(52) U.S. Cl.
CPC .. *A61B 2090/103* (2016.02); *A61M 2025/028* (2013.01); *A61M 2039/025* (2013.01); *A61M 2210/0687* (2013.01)

(56) References Cited

U.S. PATENT DOCUMENTS

| | | | | |
|---|---|---|---|---|
| 6,356,792 | B1* | 3/2002 | Errico | A61N 1/0534 606/129 |
| 7,004,948 | B1 | 2/2006 | Pianca et al. | |
| 7,604,644 | B2* | 10/2009 | Schulte | A61N 1/0539 606/129 |
| 8,182,460 | B2 | 5/2012 | Kaplitt et al. | |
| 8,313,453 | B2 | 11/2012 | Carbunaru et al. | |
| 8,974,380 | B2* | 3/2015 | Michaeli | A61B 17/0293 600/219 |
| 9,345,878 | B2 | 5/2016 | Digiore et al. | |
| 9,381,357 | B2 | 7/2016 | Min et al. | |
| 9,474,896 | B2 | 10/2016 | Lopez | |
| 2005/0143799 | A1* | 6/2005 | Black | A61B 5/6864 607/116 |
| 2005/0143800 | A1* | 6/2005 | Lando | A61N 1/0539 607/116 |
| 2005/0182425 | A1 | 8/2005 | Schulte et al. | |
| 2010/0145357 | A1* | 6/2010 | Lane | A61N 1/0539 606/129 |
| 2010/0161018 | A1 | 6/2010 | Sauter-Starace et al. | |
| 2010/0179563 | A1* | 7/2010 | Skakoon | A61B 5/6864 606/129 |
| 2011/0276056 | A1 | 11/2011 | Grigsby et al. | |
| 2011/0276117 | A1* | 11/2011 | Lando | A61N 1/0539 607/116 |
| 2013/0184793 | A1* | 7/2013 | Lando | A61N 1/0539 607/116 |
| 2013/0197472 | A1* | 8/2013 | Skakoon | A61B 5/6864 604/500 |
| 2014/0276416 | A1* | 9/2014 | Nelson | A61M 25/02 604/151 |
| 2014/0276418 | A1* | 9/2014 | Nelson | A61M 5/158 604/151 |
| 2016/0166326 | A1 | 6/2016 | Bakker et al. | |

OTHER PUBLICATIONS

P. van den Munckhof, et al., "Postoperative Curving and Upward Displacement of Deep Brain Stimulation Electrodes Caused by Brain Shift", Neurosurgery, 67:49-54, Jul. 2010.

* cited by examiner

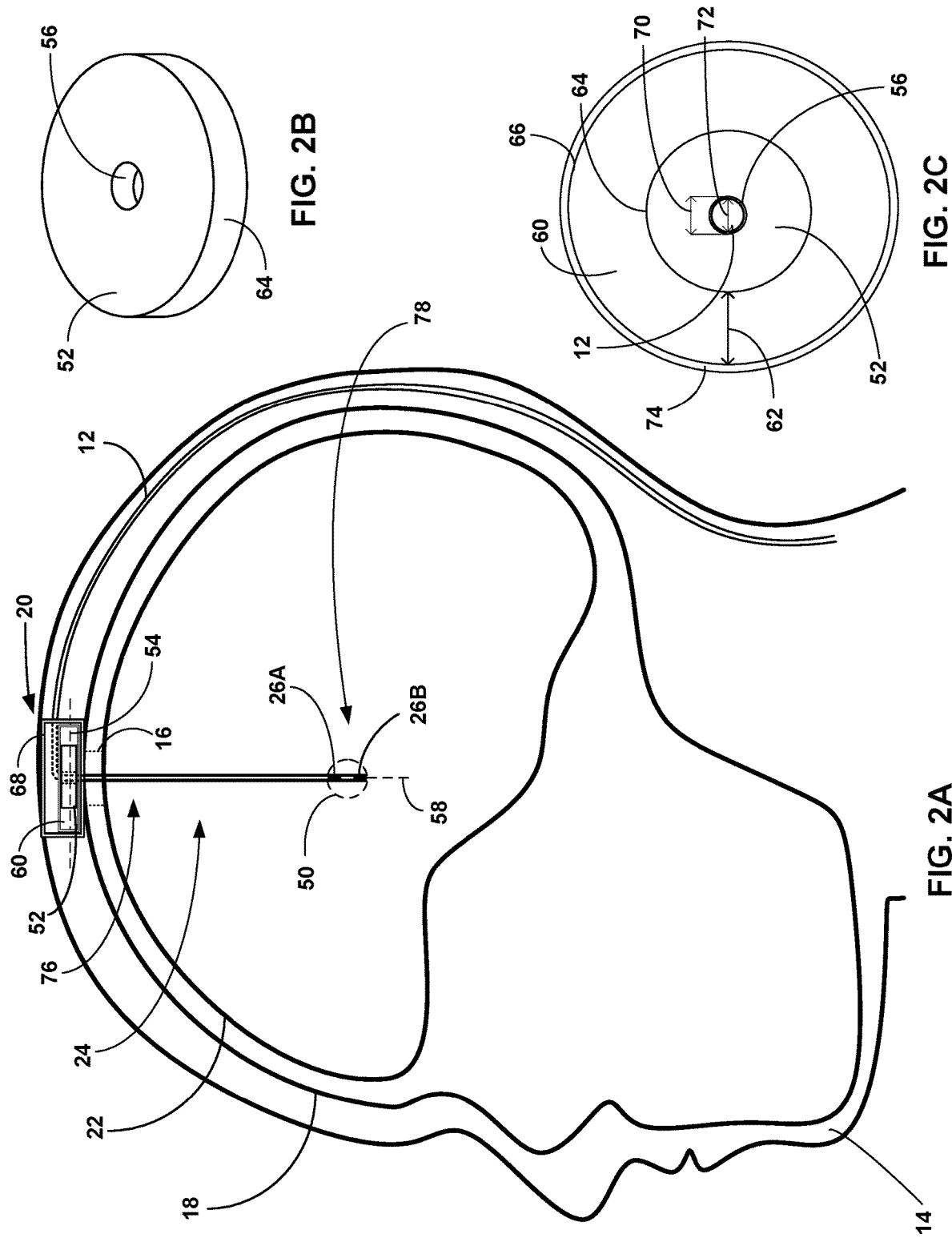

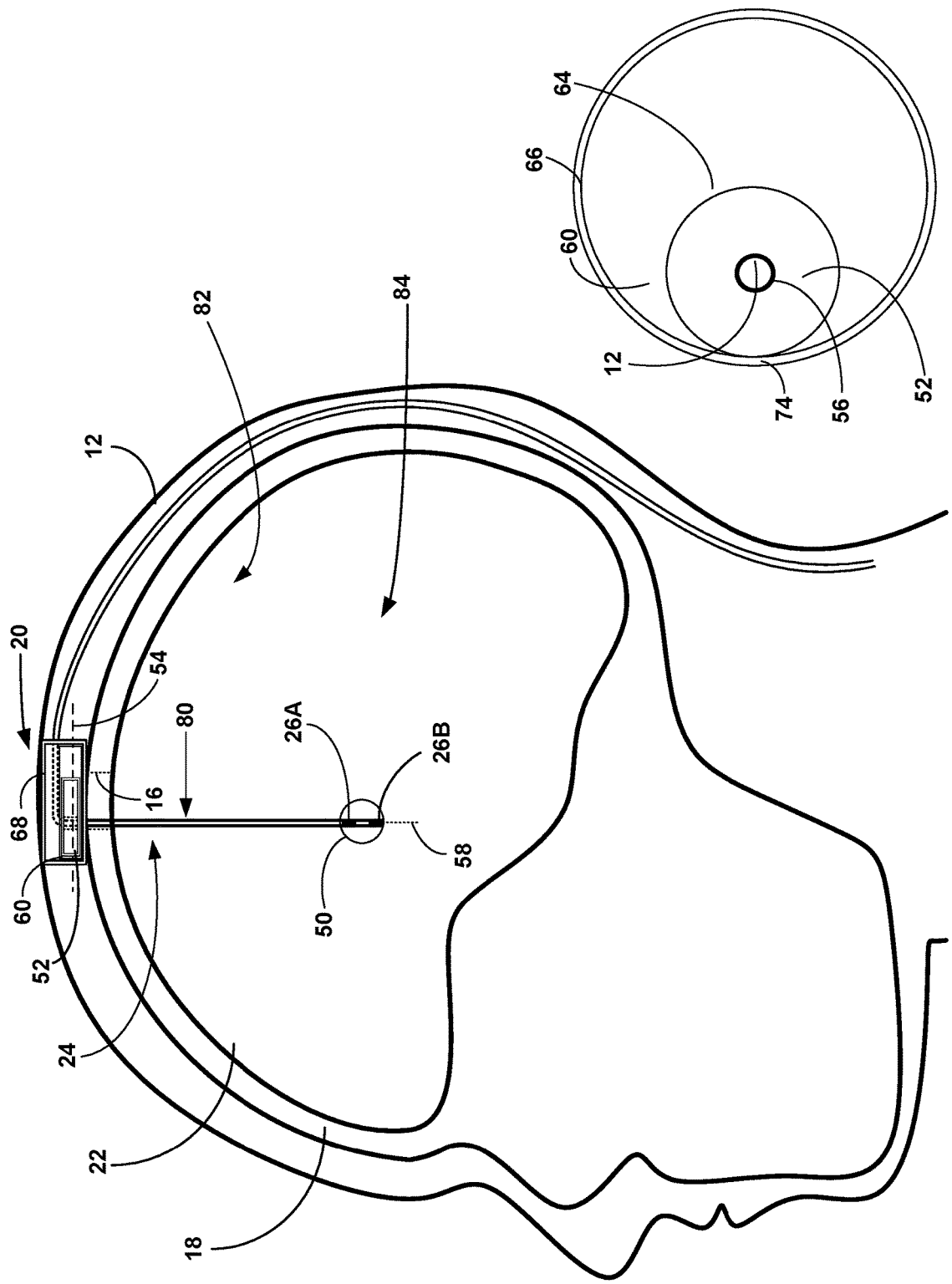

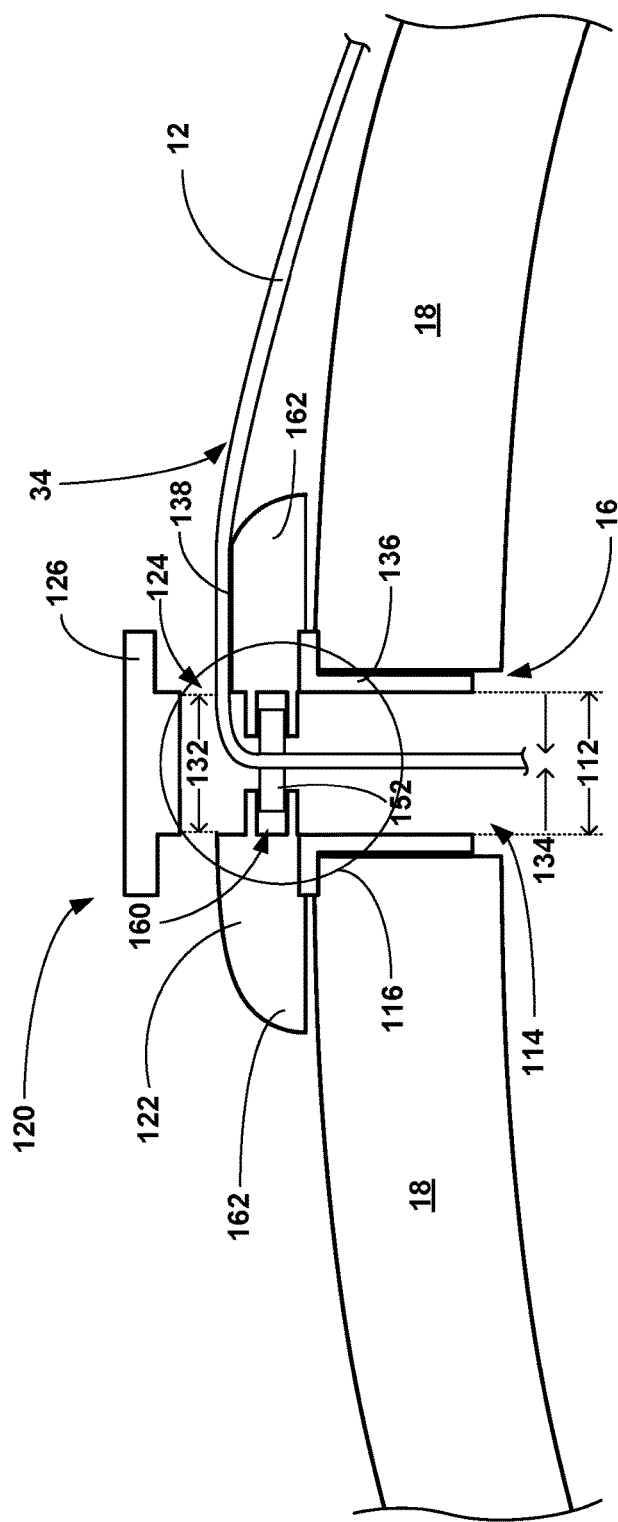
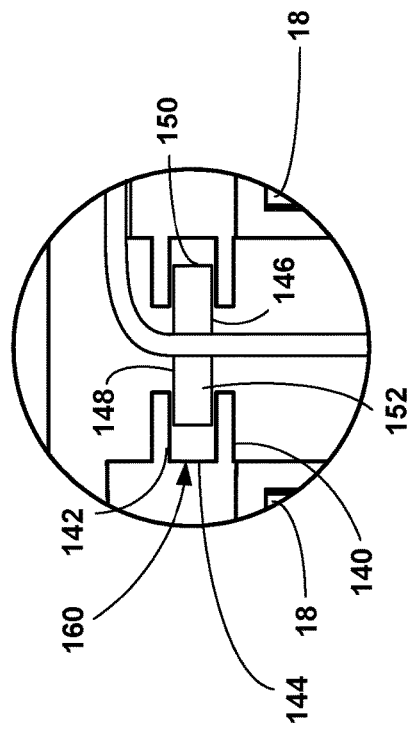
FIG. 5A
FIG. 5B

SHIFTING BURR CAP ASSEMBLY

TECHNICAL FIELD

The disclosure relates to burr cap assemblies for use with an elongate member to be implanted in the brain.

BACKGROUND

In some medical systems, one or more elongate members may be implanted in a brain. For example, elongate members may be one or more leads that are implanted in a brain of a patient. For another example, elongate member may be a catheter or another therapeutic delivery device that delivers an agent to a brain. The elongate member may access regions of the brain through one or more burr holes formed through the patient's cranium. A burr cap assembly, which is positioned within a burr hole, may be used to retain the elongated medical device relative to the burr hole, as well as substantially plug an opening in the burr hole.

SUMMARY

This disclosure describes burr cap assemblies that permit an elongate member shifting in response to post-implantation brain shift, and methods of use and manufacture of the burr cap assemblies. A burr cap assembly may be at least partially inserted into a burr hole within the cranium of a patient. The burr cap assembly may enable an elongate member to be inserted through the burr cap assembly to access a brain of the patient. The elongate member may be a lead, a catheter, a fiber optic cable, or another similar elongated medical device that is implanted in a brain for a relatively long period of time (e.g., enough time for the brain to shift post-implantation). In some examples, fluids and matter of the brain may shift after a medical procedure involving insertion of the elongate member into the brain of a patient as the brain adjusts to and recovers from the insertion procedure. To avoid a distal portion of the elongate member migrating partially or fully away from a target site within the brain, a shifting member of the burr cap assembly may be configured to enable the elongate member to move with the shifting fluid and matter of the brain. For example, the shifting member of the burr cap assembly may be configured to move within a cavity defined by the burr cap assembly. The shifting member may be configured to move in a direction that is substantially perpendicular to a longitudinal axis of the distal portion of the elongate member. The shifting member may at least partially retain the elongate member, so as the shifting brain applies forces upon the elongate member, the elongate member and the shifting member may move in unison within the cavity.

In some examples, a burr cap assembly may include a burr cap assembly configured to be positioned at least partially within a burr hole in a cranium of a patient, the burr cap assembly defining a cavity and being configured to enable implantation of at least a portion of an implantable medical elongate member into a brain of the patient through the burr cap assembly, the burr cap assembly including a member positioned within the cavity of the burr cap and defining at least one opening to enable passage of at least a portion of the implantable medical elongate member into the brain of the patient, the member being configured to move within the cavity relative to the burr cap within at least one dimension of a plane that is substantially perpendicular to a longitudinal axis of at least a portion of the implantable medical elongate member In some examples, a medical system may include a burr cap assembly configured to be positioned at least partially within a burr hole in a cranium of a patient. The burr cap assembly may define a cavity. The burr cap assembly may include a member positioned within the cavity of the burr cap assembly. The member may define at least one opening. The member may be configured to move within the cavity relative to the burr cap assembly within at least one dimension of a plane that is substantially perpendicular to a longitudinal axis of at least a portion of the implantable medical elongate member. The medical system may further include an implantable medical elongate member. At least a portion of the implantable medical elongate member is configured to be implanted into a brain of the patient through both the burr cap assembly and the at least one opening of the member. The burr cap assembly may comprise a cover configured to retain the implantable medical elongate member as the implantable medical elongate member enters the burr cap assembly. The cover may be configured to substantially seal the burr cap.

In some examples, a method of an apparatus shifting in response to brain shift may include: in a burr cap assembly positioned at least partially within a burr hole in a cranium of a patient, moving a member, through which at least a portion of an implanted medical elongate member extends into the brain of the patient, within a cavity defined by the burr cap assembly, in at least one dimension of a plane that is substantially perpendicular to a longitudinal axis of the at least a portion of the implantable medical elongate member, to move the at least a portion of the implantable medical elongate member in response to a force applied to the member by the implantable medical elongate member following implantation of the at least a portion of the implantable elongate member in the brain of the patient.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 2A is a conceptual cross-sectional illustration of an elongate member extending through a base of a burr cap assembly that is inserted in a burr hole formed in a cranium of a patient, in accordance with an example of this disclosure.

FIG. 2B is a conceptual perspective illustration of an example shifting member of the burr cap assembly of FIG. 2A, in accordance with an example of this disclosure.

FIG. 2C is a conceptual cross-sectional plan illustration of the burr cap assembly of FIG. 2A, in accordance with an example of this disclosure.

FIG. 3A is a conceptual cross-sectional illustration of an elongate member extending through a base member of a burr cap assembly that is inserted in a burr hole formed in a cranium of a patient after the elongate member has shifted towards the front of the cranium, in accordance with an example of this disclosure.

FIG. 3B is a conceptual cross-sectional plan illustration of the burr cap assembly of FIG. 3A, in accordance with an example of this disclosure.

FIG. 5A is a conceptual cross-sectional side view of an example burr cap assembly that is inserted in a burr hole with an example shifting member in a cavity of a base member of the burr cap assembly in accordance with another example of the disclosure.

FIG. 5B is a conceptual cross-sectional side view illustrating the shifting element in the cavity of FIG. 5A in greater detail.

DETAILED DESCRIPTION

Figure 1:
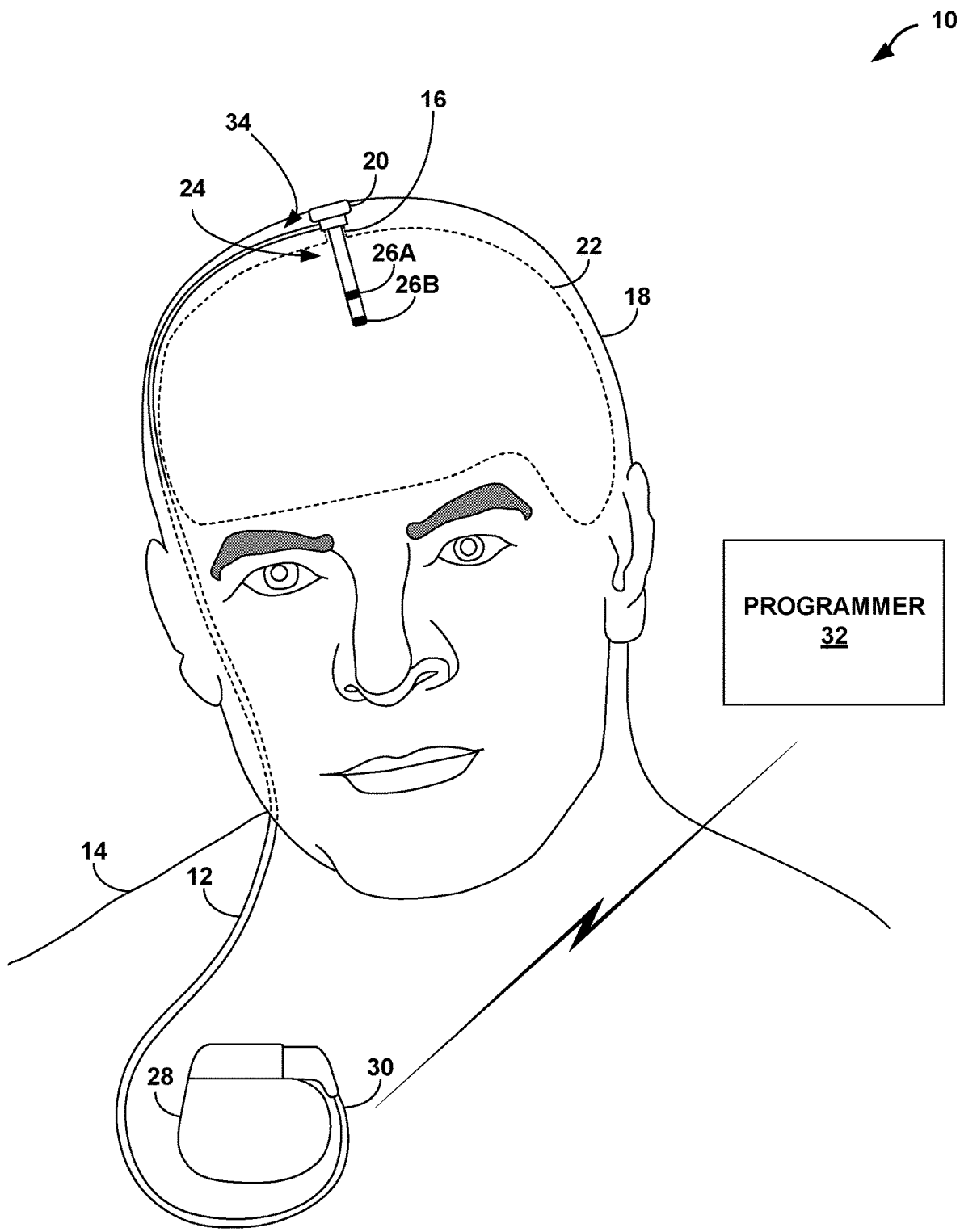
FIG. 1 is a conceptual illustration of an elongate member implanted in a brain of a patient through a burr hole formed in a cranium of the patient.

The features and techniques described herein are useful in medical device systems, which may include implantable medical elongate members and implantable medical devices. In some examples, the features and techniques described herein may be used in systems with one or more implantable electrical stimulation elongate members (leads) and implantable medical devices that deliver electrical stimulation therapy to a patient's brain (e.g., deep brain stimulation (DBS)) via the elongate members. In other examples, the features and techniques described herein may be used in systems with one or more implantable catheter elongate members that delivery agents (e.g., therapeutic agents) to a patient's brain via a lumen in the catheter elongate members, or system with one or more fiber optic cable elongate members that delivery energy to a patient's brain. One or more elongate members may be implanted through one or more burr holes within the cranium of the patient. For example, the features and techniques described herein may be used in systems that employ one or more burr caps.

Creating one or more burr holes in the cranium of a patient, filling the burr hole(s) with one or more burr caps, and inserting one or more implantable medical elongate members therein may cause the location of a portion of the brain to shift relative to the cranium during and/or after the implantation procedure. For example, the brain of a patient may experience "brain shift" as a result of implantation procedure, as fluids and/or other matter of a brain react to the implantation procedure. In some examples, brain shift may result from the craniotomy alone regardless of the duration of surgery or the components implanted or inserted into the brain following the craniotomy. Brain shift may be the result of a loss of pressure gradient across the dura mater and loss of cerebrospinal fluid (CSF) during the procedure. In some examples, subdural air may appear at the frontal cortex after procedures where brain shift has occurred.

Recovery from brain shift may result in the brain settling toward a stable position may occur over the course of a few days or weeks as the patient's body heals from the implantation procedure and adjusts to the implanted system. If unaccounted for, brain shift may cause components of an implanted system to migrate away from an intended initial implanted location. For example, where the elongate member is a DBS lead with distal electrodes, brain shift may result in one or more implanted DBS leads being pulled axially back towards respective burr holes in the cranium of the patient, such that the distal electrodes of the DBS lead may migrate axially away from a target site. Alternatively, where the elongate member is a catheter with an output port for delivering a therapeutic agent, brain shift may result in the output port migrating away from the target tissue that is to receive that agent. As yet another example, where the elongate member is a device carrying one or more channel (s) for delivering energy (e.g., optical fibers for delivering optical energy), brain shift may result in the energy-emitting surfaces being relocated to that the energy is no longer directed (or is directed with less efficiency) to the target tissue.

Aspects of the disclosure relate to an implantable medical device that includes a burr cap assembly that permits an elongate member to shift in response to brain shift. By permitting elongate member shift, the burr cap assembly may reduce migration of a distal portion of the elongate member that may be configured to monitor or delivery therapy (e.g., with electrodes where elongate member is an implanted DBS, or with output ports to deliver agents where elongate member is a catheter) to a target location in the brain. In some examples, target locations of a brain may be relatively localized, such that any migration of the distal portion of the elongate member may impact the ability for the elongate member to monitor or delivery therapy, therein result in a loss of efficacy. Therefore, in some examples, by permitting an elongate member to shift in response to brain shift, a burr cap assembly may reduce the likelihood of a loss of therapy or monitoring efficacy as a result of elongate member migration.

The burr cap assembly may define a cavity and a shifting member within the cavity. This burr cap assembly may facilitate shifting of one or more elongate members implanted within a brain of a patient while the burr cap assembly is securely attached to a cranium of a patient. For example, the burr cap assembly may permit a more proximal portion of the elongate member that extends through the burr cap assembly to shift laterally in one or more directions in response to brain shift such that axial and/or lateral shifting of a distal portion of the elongate member implanted within the brain is reduced.

The one or more implantable elongate members may be implanted through one or more burr holes formed in the cranium of the patient (e.g., where a burr cap assembly is at least partially inserted within each burr hole). The burr cap assembly may be fastened to the cranium while being at least partially inserted within the burr hole. In some examples, a burr cap may secure the one or more implantable elongate member(s) to the cranium of the patient, such that it is difficult or impossible to remove or displace the portion of the implantable elongate member that is within the brain of the patient without disassembling the burr cap assembly. The shifting member may float or translate within the cavity of the burr cap assembly. For example, the shifting member may move laterally in one or more directions generally along a plane of the cavity of the burr cap assembly. Providing an implantable medical device that securely attaches an implantable elongate member to a cranium of a patient while allowing the elongate member to shift with the brain inside the cranium may provide benefits in ensuring an implantable elongate member within the brain of a patient has greater stability.

As discussed above and herein, an elongate member as received and secured by the burr cap assembly may be a lead with electrodes at a distal end to provide electrical stimulation to and/or monitoring of a brain of a patient. Alternatively, an elongate member may be a catheter for delivery a therapeutic agent or some other agent (e.g., a transfecting agent). Further details regarding elongate member being a catheter may be found in a commonly-assigned U.S. Patent entitled "INFUSION DEVICE AND METHOD FOR INFUSING MATERIAL INTO THE BRAIN OF A PATIENT," U.S. Pat. No. 8,182,460. In certain examples, the elongate member may be a device that carries one or more optical fibers for delivering energy to the target site in the brain, or some other therapy delivery device or monitoring device for the brain having an elongated structured adapted for insertion via a burr hole in the cranium of a patient.

FIG. 1 is a conceptual illustration of a part of an implanted therapy system 10, which includes implantable medical elongate member 12 implanted within patient 14 through a burr hole 16 defined through cranium 18 of patient 14. Therapy system 10 further includes burr cap assembly 20, which is configured to substantially fix elongate member 12 relative to cranium 18 as elongate member 12 enters burr cap assembly 20. Further, burr cap assembly 20 is configured to substantially cover and plug burr hole 16. Burr cap assembly 20 may include a burr cap as described herein that is at least partially mountable within burr hole 16. Securing elongate member 12 at a substantially fixed position relative to cranium 18 as elongate member 12 enters burr cap assembly 20 may help secure a portion (e.g., a distal section 24) of elongate member 12 that is configured to deliver therapy to a target tissue site in brain 22 of patient 14. As described in further detail below, burr cap assembly 20 includes one or more components that enable some or all of distal section 24 of elongate member 12 that is implanted in brain 22 to shift relative to burr hole 16.

Enabling some or all of an implanted distal section 24 of elongate member 12 to shift relative to burr hole 16 may be useful for various purposes, such as for compensating for naturally-occurring post-implantation brain shift. Components of burr cap assembly 20 may enable some or all of distal section 24 of elongate member 12 to shift in a direction generally radial to elongate member 12, i.e., in a lateral direction, as elongate member 12 enters cranium 18. Enabling some or all of distal section 24 of elongate member 12 to shift in a generally radial direction may reduce the possibility of one or more distal components 26A, 26B (collectively "components 26") carried at a distal portion of elongate member 12 axially retracting towards burr hole 16 as a result of brain shift. In some examples, distal components 26 may be electrodes where elongate member 12 is a lead, distal components 26 may be one or more output ports to one or more lumens where elongate member 12 is a catheter, or distal components 26 may be one or more emitting surfaces where elongate member 12 is an optical fiber. Other examples of distal components 26 for other examples of elongate members 12 are also possible.

Implanted therapy system 10 is depicted within FIG. 1 as including one elongate member 12 inserted through one burr hole 16 using one burr cap assembly 20. However, in some examples, implanted therapy system 10 may include two elongate members 12 (not depicted), such that distal section 24 of a first elongate member 12 is implanted in one hemisphere of brain 22 and distal section 24 of a second elongate member 12 is implanted in the other hemisphere of brain 22. Implanting separate elongate members 12 into separate hemispheres of brain 22 may enable implanted therapy system 10 to more effectively diagnose, monitor, or otherwise treat some medical conditions. The two elongate members 12 may be implanted through two separate burr holes 16 using respective burr cap assemblies 20. Alternatively, the two elongate members 12 may be implanted through a single burr hole 16. Though FIG. 1 depicts a single elongate member 12, burr hole 16, and burr cap assembly 20 for purposes of clarity, it is to be understood that the concepts described herein are applicable to an implanted therapy system 10 that utilizes two elongate members 12 inserted through one or two burr holes 16 using one or two burr cap assemblies 20, such that some or all of distal sections 24 of one or both elongate members 12 can shift in a generally radial direction with one or two burr holes 16 as a result of one or two burr cap assemblies 20.

Elongate member 12 can be any suitable medical member that is configured to deliver therapy to one or more target tissue sites within patient 14. For example, elongate member 12 may be configured to deliver therapy from a medical device to the one or more target tissue sites and/or elongate member 12 may be configured to sense one or more physiological parameters of patient 14. For example, medical system 10 may include an implantable medical device (IMD) 28 configured to deliver electrical stimulation therapy to and/or sense physiological signals from brain 22 of patient 14 through elongate member 12 where elongate member 12 is a lead. More particularly, IMD 28 may deliver electrical stimulation and sense electrical signals via electrodes distal components 26 on distal section 24 of lead elongate member 12. The stimulation and signals may be conducted between electrode distal components 26 and IMD 28 by conductors within lead elongate member 12, where the conducts are electrically connected to 1 MB 28 by connectors at proximal end 30 of lead elongate member 12. In examples where implantable medical system 10 includes two elongate members 12, both elongate members may connect to the same 1 MB 28 or to separate IMDs.

IMD 28 may include electronics and other internal components. In one example, IMD 28 include processing circuitry, memory, signal generation circuitry, sensing circuitry, telemetry circuitry, and a power source. In general, memory of an 1 MB 28 may include computer-readable instructions that, when executed by processing circuitry of the IMD, cause it to perform various functions attributed to the device herein. For example, processing circuitry of an 1 MB 28 may control signal generation circuitry and sensing circuitry according to instructions and/or data stored on memory to deliver therapy to patient 14, sense physiological signals of the patient, and perform other functions related to treating one or more conditions of the patient with IMD 28.

Such signal generation circuitry of 1 MB 28 may generate electrical stimulation that is delivered to patient 14 via distal components 26 on one or more elongate members 12, in order to provide neurostimulation therapy such as, for example, DBS. This sensing circuitry of 1 MB 28 may monitor electrical signals from electrodes on one or more elongate members 12 of IMD 28 in order to monitor electrical activity of patient 14, e.g., to monitor electrical signals generated by brain 22, such as local field potentials (LFPs) or other neurological signals. Telemetry circuitry of IMD 28 may include any suitable hardware, firmware, software or any combination thereof for communicating with another device, such as programmer 32. Under the control of processing circuitry of IMD 28 the telemetry circuitry may receive downlink telemetry from and send uplink telemetry to programmer 32 with the aid of an antenna, which may be internal and/or external.

Programmer 32 may be a handheld computing device, computer workstation, or networked computing device. Programmer 32 may include electronics and other internal components necessary or desirable for executing the functions associated with the device. In one example, programmer 32 includes processing circuitry and memory, as well as a user interface, telemetry circuitry, and power source.

As shown in FIG. 1, medical device system 10 includes IMD 28 with elongate member 12 entering through cranium 18 and implanted within brain 22 of patient 14 to deliver deep brain stimulation (DBS). One or more distal components 26 on distal section 24 of elongate member 12 provide monitoring or therapy (e.g., transfecting agent, fiber optic energy, or electrical stimulation pulses or other waveforms) to surrounding anatomical regions of brain 22 in a therapy that may alleviate a condition of patient 14. In some examples, more than one elongate member 12 may be implanted within brain 22 of patient 14 to stimulate, monitor, or otherwise treat multiple anatomical regions of brain 22.

DBS may be used to treat dysfunctional neuronal activity in brain 22 which manifests as diseases or disorders such as, for example, Huntington's Disease, Parkinson's Disease, or movement disorders. Symptoms of these diseases can be lessened or eliminated with electrical stimulation therapy. Certain anatomical regions of brain 22 are responsible for producing the symptoms of such brain disorders. As one example, stimulating an anatomical region, such as the Substantia Nigra, in brain 22 may reduce the number and magnitude of tremors experienced by patient 14. Other anatomical regions may include the subthalamic nucleus, globus pallidus interna, ventral intermediate, and zona inserta. Anatomical regions such as these are targeted by the clinician during the implantation of elongate member 12. In other words, the clinician may attempt to position distal section 24 of elongate member 12, including the one or more distal components 26, as close to these regions as possible.

FIG. 2A is a conceptual diagram illustrating an example burr cap assembly 20 facilitating the implantation of one or more elongate members 12 into brain 22 of a patient 14. Elongate member 12 includes a distal section that extends from burr cap assembly 20 into brain 22. The burr cap assembly 20 may be configured to enable adjacent portion 76 of distal section 24 of elongate member 12 that is distal and adjacent to the burr cap assembly to shift in response to naturally-occurring post-implantation recovery from brain shift such that distal portion 78 that includes distal components 26 does not shift relative to target site 50. Permitting adjacent portion 76 of distal section 24 of elongate member 12 that is adjacent to burr cap assembly 20 to shift, e.g., radially, may prevent or reduce axial shifting of a more distal portion 78 of distal section 24 relative to the brain, thus potentially leading to loss of therapy. Hence, configuring burr cap assembly 20 to enable adjacent portion 76 of distal section 24 of elongate member 12 to shift, e.g., radially, within brain 22 may increase the likelihood that implanted distal components 26 at the more distal portion 78 will stay substantially positioned at target site 50 within brain 22 (e.g., rather than migrating away from target site 50, such as migrating axially back towards burr hole 16). Increasing the likelihood that implanted distal components 26 will stay at target site 50 within brain 22 may increase the ability of medical system 10 to providing efficacious treatment and/or monitoring.

Burr cap assembly 20 may include a first member that shifts in response to brain shift while retaining elongate member 12, said first member hereinafter referred to as shifting member 52. In other examples, shifting member 52 may be a separate component than burr cap assembly 20, configured to move relative to a substantially stationary burr cap assembly 20 once burr cap assembly 20 is inserted in cranium 18 of patient 14. Shifting member 52 may be a substantially rigid, unitary component. For example, FIG. 2B is a conceptual perspective illustration of shifting member 52. As depicted in FIG. 2B, shifting member 52 may be generally disk- or plate-shaped, with a major surface area that is substantially circular (e.g., such that shifting member 52 is a substantially circular plate). In some examples, shifting member 52 may be substantially solid (e.g., not hollow). Shifting member 52 may be configured to retain an implantable elongate member 12. Shifting member 52 may include at least one opening to enable passage of at least a portion of elongate member 12. Specifically, shifting member 52 may include hole 56 to enable passage of distal section 24 into brain 22 of patient 14. For example, looking to the conceptual diagram of FIG. 2C illustrating a cross-sectional view of the burr cap assembly 20 along plane 54, elongate member 12 is within hole 56 generally in the middle of shifting member 52. As depicted in FIG. 2A, plane 54 is substantially perpendicular to longitudinal axis 58 of elongate member 12. In this way, the opening/hole 56 of shifting member 52 may eliminate/substantially restrict relative movement between shifting member 52 and adjacent portion 76 of distal section 24 of elongate member 12 (e.g., the section of elongate member 12 immediately distal and adjacent to burr cap assembly 20 as elongate member 12 passes through hole 56 defined by shifting member 52 in a direction substantially perpendicular to longitudinal axis 58 of the implantation of distal section 24 of elongate member 12).

Shifting member 52 may be configured to radially retain elongate member 12, such that elongate member 12 may not radially move relative to shifting member 52. Further, shifting member 52 may be configured to radially retain elongate member 12 such that elongate member 12 may only move relative to burr hole 16 when shifting member 52 moves relative to burr hole 16 (e.g., where both elongate member 12 and shifting member 52 move in conjunction along plane 54). Shifting member 52 may radially retain elongate member 12 as a result of hole 56, as diameter 70 of hole 56 may be just nominally larger than outer diameter 72 of elongate member 12.

Further, in some examples, shifting member 52 may be configured to axially retain elongate member 12, such that elongate member 12 may not axially move relative to shifting member 52 unless shifting member 52 moves axially along longitudinal axis 58. For example, shifting member 52 may utilize a jaw mechanism (e.g., a mechanism that clamps down on elongate member 12 from two or more directions) to axially retain elongate member 12. The jaw mechanism may include a Stimloc mechanism, a wrench mechanism, a mechanical clip mechanism, or the like. Following an implantation procedure using a jaw mechanism, the wound may resolve and self-seal over a period of time (e.g., the subsequent two-six months following the implantation procedure). In other examples, shifting member 52 may axially retain elongate member 12 as a result of diameter 70 of hole 56 being substantially similar to diameter 72 of elongate member 12, such that there is an interference fit between shifting member 52 and elongate member 12. In other examples, elongate member 12 may be bonded to shifting member 52, e.g., with an adhesive, once elongate member 12 is navigated to target site 50. Other mechanisms for shifting member 52 to axially retain elongate member 12 are also possible.

Shifting member 52 may be an implantable component that is configured to enable elongate member 12 to shift in a direction that is generally radial to elongate member 12 as elongate member 12 enters cranium 18 and generally perpendicular to longitudinal axis 58 of distal section 24 of elongate member 12. For example, shifting member 52 may be configured to shift in at least one dimension along plane 54 that is substantially perpendicular to longitudinal axis 58 of distal section 24 of elongate member 12. As discussed in greater detail below, shifting member 52 may be configured/sized to fit within cavity 60 of burr cap assembly 20, such that an outer width/diameter of shifting member 52 is smaller than an inner width/diameter of cavity 60 of burr cap assembly 20. In some examples, shifting member 52 may be configured to shift in two or more dimensions along plane 54. For example, shifting member 52 and cavity 60 may be dimensioned such that cavity 60 restricts movement of shifting member 52 in a dimension or direction that is substantially parallel to the longitudinal axis of elongate member 12 within burr cap assembly 20. Shifting member 52, in other examples, may shift in any direction within plane 54.

Looking back to FIG. 2A, shifting member 52 may be configured to enable distal section 24 of elongate member 12 to shift as a result of shifting member 52 being configured to shift in one or more dimensions of plane 54 while shifting member 52 retains elongate member 12. Put differently, shifting member 52 may enable adjacent portion 76 of distal section 24 of elongate member 12 to shift by itself shifting relative to burr hole 16 as shifting member 52 radially retains elongate member 12, such that both shifting member 52 and elongate member 12 may shift in unison relative to burr hole 16 while distal portion 78 of elongate member 12 remains substantially stationary relative to target site 50. For example, after distal section 24 of elongate member 12 is inserted at least partially in brain 22, fluids and matter of brain 22 may exert forces upon elongate member 12 (e.g., as a result of recovery from brain shift as described herein). In response to these forces upon elongate member 12, elongate member 12 may in turn apply a force to shifting member 52, causing shifting member 52 and elongate member 12 to shift in conjunction (e.g., shift within cavity 60 as described herein). In one example, an outer width or diameter of shifting member 52 relative to an inner width or diameter of cavity 60 may define an amount that shifting member 52 and elongate member 12 may shift relative to burr hole 16.

The forces of the fluid and matter of brain 22 may be generally perpendicular to longitudinal axis 58 of elongate member 12. The forces may be relatively unpredictable, such that it may be difficult or impossible for a clinician to determine either before or during a procedure the direction or magnitude of the post-implantation forces. Therefore, it may be advantageous to configure shifting member 52 to shift with elongate member 12 in response to post-implantation forces, as this mutual shifting may reduce or eliminate the chance of adjacent portion 76 of distal section 24 of elongate member 12 (and/or distal portion 78 of distal section 24 of elongate member 12) radially shifting relative to shifting member 52 (e.g., as such radial shifting of distal section 24 of elongate member 12 relative to shifting member 52 may result in elongate member 12 having to travel a longer path to get to target site 50, causing electrodes 26 to axially retract some distance towards burr hole 16 relative to an initial implantation position, thereby potentially decreasing efficacy of medical device system 10).

Shifting member 52 may be made from any suitable material, such as, but not limited to, titanium, biocompatible polymers, or other biocompatible materials. In some examples, shifting member 52 comprises a radiopaque material, such that shifting member 52 may be detected by medical imaging after shifting member 52 has been implanted. Configuring shifting member 52 (in conjunction with cavity 60) such that an amount of post-implantation shift of shifting member 52 may be identified and/or quantified may improve the ability of a clinician to monitor the amount of recovery from brain shift and determine treatment options.

Shifting member 52 may be sized to "float," i.e., move, within cavity 60. Cavity 60 may be a predetermined unobstructed area with rigid walls that define one or more dimensions (e.g., radial direction on plane 54) in which shifting member 52 may move. Cavity 60 may be defined by burr cap assembly 20. In some examples, cavity 60 is defined by a burr cap itself, and in other examples, cavity 60 may be defined by a retention member that is connected to the burr cap. Cavity 60 and shifting member 52 may be configured together to define a gliding joint that enables shifting member 52 and adjacent portion 76 of distal section 24 of elongate member 12 to radially shift in unison relative to burr hole 16. The walls of cavity 60 may be substantially rigid to limit travel of shifting member 52 within burr cap assembly 20. For example, shifting member 52 may be sized to have a major surface that smaller, e.g., in one dimension, two dimensions, or all dimensions, than a size of cavity 60, such that shifting member 52 may move within cavity 60 in response to force exerted on elongate member 12 by brain shift. Cavity 60 may be configured to permit substantially radial shifting of adjacent portion 76 of distal section 24 of elongate member 12 in one or more directions perpendicular to longitudinal axis 58 of elongate member 12 in which shifting member 52 may shift. A rigid wall or walls of cavity 60 may define bounds of movement of shifting member 52.

Cavity 60 may define one or more dimension in which shifting member 52 may move by defining a space into which shifting member 52 may shift. For example, looking to FIG. 2C, cavity 60 may define space 62 between outer wall 64 of shifting member 52 and wall 66 of cavity 60. Wall 66 of cavity may be defined by structure 74. As described above, structure 74 is part of burr cap assembly 20, whether formed as the burr cap itself or a retention member that is attached to burr cap. Cavity 60 may define a substantially planar channel. For example, cavity 60 may be substantially cylindrical. In some examples, both shifting member 52 and cavity 60 may define substantially circular cross sections as depicted in FIG. 2B, such that space 62 is relatively constant around shifting member 52 before shifting member 52 has moved. In this example, shifting member 52 is shaped as a substantially circular disk that resides within a larger, substantially circular cavity 60 of burr cap assembly 20.

For example, cavity 60 may be configured to enable shifting member 52 to slide or move over to wall 66 of cavity 60, thereby moving in a dimension to occupy space 62. As depicted, cavity 60 may define space 62 (or an area substantially similar to space 62) 360° around shifting member 52 on plane 54 substantially perpendicular to elongate member 12, such that cavity 60 is configured to enable shifting member 52 to move through space 62 in any dimension on plane 54. In other examples, cavity 60 may only define space 62 in a subset of directions or dimensions, therein configuring shifting member 52 to only move in predetermined dimension on plane 54.

Conversely, cavity 60 may be configured to substantially eliminate movement of shifting member 52 in an axial direction along longitudinal axis 58 of elongate member 12. Cavity 60 may be configured to substantially eliminate movement of shifting member 52 along longitudinal axis 58 by defining substantially no space for shifting member 52 to move into along the longitudinal axis 58. In this manner, shifting member 52 can move laterally but not significantly move axially.

Cavity 60 may define a different space 62 for different applications. For example, space 62 may be smaller for patients 14 with relatively smaller craniums 18, or for patients 14 that are undergoing a relatively more invasive procedure. Configuring space 62 to only be as large as necessary to allow elongate member 12 to shift such that electrodes 26 remain in target area 50 may provide size benefits for burr cap assembly 20, as it may be generally preferable to keep the sizes of implantable devices as small as practicable for comfort and functionality. Further, in some examples, a clinician may know a general dimension in which brain shift may occur. In such examples, cavity 60 may only define space 62 along this dimension. Where a clinician may know a general dimension in which brain shift may occur, it may be advantageous to configure cavity 60 to only define space 62 along this dimension, as this may enable cavity 60 to define a larger space 62 therein, allowing for increased shifting (and potentially increasing a margin for error) and/or this may enable a reduction of the size of cavity, therein potentially reducing the size of burr cap assembly 20. In some examples, burr cap assembly 20 may be manufactured with a variety of cavity 60 sizes and/or shifting member 52 sizes to enable a clinician to determine an allowable magnitude of shifting by assembling a specific combination of components of burr cap assembly 20 that define this determined magnitude of shifting. For example, burr cap assembly 20 may be manufactured and delivered with, e.g., a small, medium, and large shifting member 52, as well as components that define, e.g., a small, medium, and large cavity 60, where each size cavity 60 securely houses each size of shifting member 52 within burr cap assembly 20 and therein defines a different amount of possible shifting, enabling a clinician to define a maximum amount of shifting during or prior to the insertion procedure.

In some examples, shifting member 52 and elongate member 12 may move in a dimension along plane 54 within cavity 60 towards the front of cranium 18. For example, FIG. 3A is a conceptual diagram illustrating shifting member 52 and elongate member 12 shifting in brain 22 towards front of cranium 18 (i.e., in an anterior or ventral direction). Shifting member 52 and adjacent portion 76 of elongate member 12 may move together in response to a first force that is applied to shifting member 52 by elongate member 12. Elongate member 12 may apply the first force to shifting member 52 in response to a second force applied to elongate member 12 by fluids of brain 22 following the implantation of elongate member 12 and/or burr cap assembly 20 (e.g., the second force applied to elongate member 12 causes elongate member 12 to apply first force to shifting member 52, such that the elongate member 12 acts as a lever translating the second force into the first force). For example, shifting member 52 and adjacent portion 76 of elongate member 12 may move together in response to force 80 exerted upon distal section 24 of elongate member 12. Shifting member 52 and elongate member 12 may shift such that electrodes 26 of elongate member 12 remain at target site 50. In some examples, the location of target site 50 may have shifted relative to cranium 18 through the process of brain shift as discussed herein, even as the specific tissue of brain 22 that is targeted for stimulation and/or analysis by electrodes 26 may remain constant (e.g., such that electrodes 26 may stay at substantially the same portion of brain 22 even as this same portion of brain 22 moves). In other examples, the location of target site 50 may have remained substantially constant relative to cranium 18 through brain shift, such that outer region 82 of brain 22 undergoes brain shift while inner region 84 undergoes minimal brain shift.

Shifting member 52 and elongate member 12 may shift as a result of shifting member 52 moving into space 62. For example, as depicted in the conceptual diagram of FIG. 3B illustrating a cross-sectional view of the burr cap assembly 20 along plane 54, shifting member 52 has shifted in a dimension until outer wall 64 of shifting member is next to wall 66 of cavity 60 (e.g., inner wall of structure 74). In some examples, shifting member 52 becomes stationary (e.g., stops moving in the dimension) once outer wall 64 of shifting member 52 contacts inner wall 66 of cavity, as member may not be able to shift any more in response to force 80. Therefore, elongate member 12 may similarly be constrained from further shifting towards the front of cranium 18 by shifting member 52.

Figures 4A, 4B:
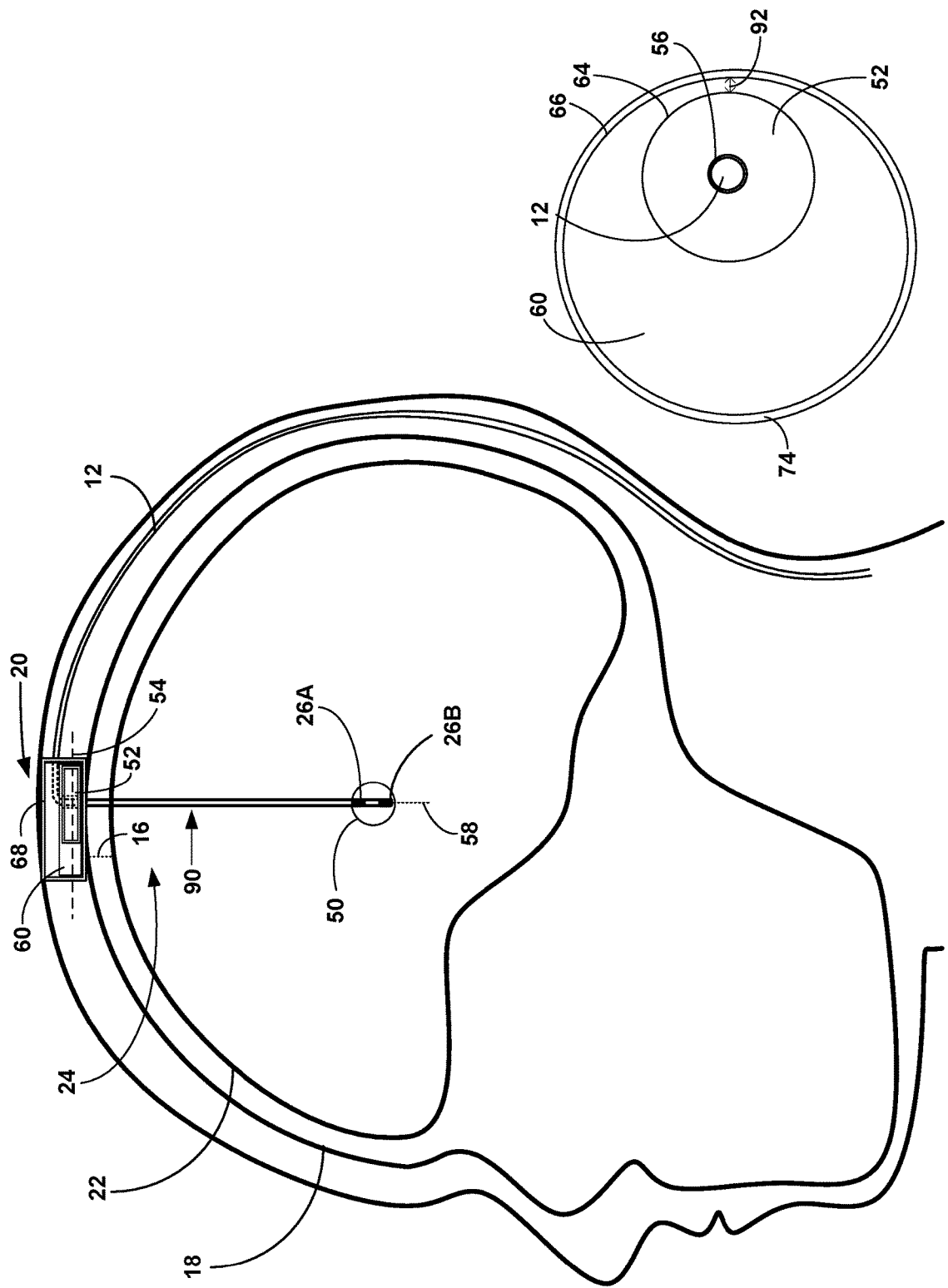
FIG. 4A is a conceptual cross-sectional illustration of an elongate member extending through a base member of a burr cap assembly that is inserted in a burr hole formed in a cranium of a patient after the elongate member has shifted towards the back of the cranium, in accordance with an example of this disclosure.
FIG. 4B is a conceptual cross-sectional plan illustration of the burr cap assembly of FIG. 4A, in accordance with an example of this disclosure.

In some examples, shifting member 52 and elongate member 12 may move in a dimension along plane 54 within cavity 60 towards the back of cranium 18 (i.e., in a posterior or dorsal direction). For example, FIG. 4A is a conceptual diagram illustrating shifting member 52 and elongate member 12 shifting in brain 22 towards back of cranium 18. Shifting member 52 and elongate member 12 may move together in response to a first force that is applied to shifting member 52. The first force may be applied to shifting member 52 in response to a second force applied to elongate member 12 by fluids of brain 22 following the implantation of elongate member 12 and/or burr cap assembly 20. For example, shifting member 52 and elongate member 12 may move within cavity 60 in response to force 90 exerted upon distal section 24 of elongate member 12. Shifting member 52 and elongate member 12 may move such that distal components 26 (e.g., electrodes, output ports to lumens, light-emitting surfaces) of elongate member 12 remain at target site 50. In some examples, location of target site 50 may have shifted relative to cranium 18 through the process of brain shift, even as the specific tissue of brain 22 that is targeted for stimulation and/or analysis by electrodes 26 may remain constant (e.g., such that electrodes 26 may stay at substantially the same portion of brain 22 even as this same portion of brain 22 moves).

In some examples, after shifting member 52 and elongate member 12 have shifted in unison within cavity 60 in response to brain shift, shifting member 52 may be remotely fixed in place to block future shifting. For example, shifting member 52 may have a locking feature (e.g., a magnetic component or mechanical component or the like) that activates or actuates to fix shifting member 52 and elongate member 12 in a location that shifting member 52 and elongate member 12 have moved to in response to brain shift. A clinician may remotely activate or actuate the locking feature to lock shifting member 52 and elongate member 12 in place. For example, the clinician may remotely activate or actuate the locking feature with a controller that remotely controls the locking feature. In some examples, a clinician may repeatedly lock and unlock shifting member 52 as desired by clinician to allow or disable further movement of shifting member 52 and elongate member 12 within cavity.

Shifting member 52 and elongate member 12 may shift as a result of shifting member 52 moving into space 62. For example, as depicted in the conceptual diagram of FIG. 4B illustrating a cross-sectional view of the burr cap assembly 20 along the plane 54, outer wall 64 of shifting member is near wall 66 of cavity 60 (e.g., interior wall of structure 74). In some examples, after an initial move of shifting member 52 and elongate member 12 as depicted in FIG. 4B, there may still be space 92 between wall 66 of cavity 60 and outer wall 64 of shifting member 52 and elongate member 12 to move into should force 90 continue to be applied.

Burr cap assembly 20 may include, in some examples, a base structure that is configured to be positioned at least partially within a burr hole in a cranium of a patient. The base structure may include or be coupled to a shaft element and may define cavity 60. Cavity 60 may be configured receive shifting member 52 to enable implantation of at least a portion of an implantable medical elongate member into brain 22 of patient 14 through burr cap assembly 20. Cavity 60 may be defined by the base structure, the shaft element or another component that is coupled to the base structure or the shaft element.

FIG. 5A is a schematic cross-sectional illustration of elongate member 12 extending through an example burr cap assembly 120, where burr cap assembly 120 is positioned at least partially within burr hole 16 through cranium 18 of patient 14. Burr cap assembly 120 may be substantially similar to burr cap assembly 20 shown in FIGS. 1A-4B, with the exceptions of any differences described herein. Burr cap assembly 120 may include at least base 122, cover 126, shaft element 136, a first member that shifts while retaining elongate member 12 in response to brain shift (e.g., shifting member 152), and cavity 160. In other examples, shifting member 152 may be a separate component to burr cap assembly 120, configured to move relative to a substantially stationary burr cap assembly 120. In some examples, burr cap assembly 120 includes a physically separate component such as a second member that defines cavity 160 (e.g., a retention member). The cross-section is taken through burr cap assembly 120, as well as through a center of elongate member 12. As shown in FIG. 2, burr cap assembly 120 includes base 122, which defines opening 124, and cover 126, which is shown in FIG. 5A in a disassembled state in which cover 126 is not mechanically coupled to base 122. Base 122 may be substantially circular in cross-section. Assembly lines are shown in FIG. 5A to illustrate how cover 126 may be aligned with base 122 such that it partially fits within opening 124 defined by base 122 to substantially cover opening 124. In some examples, the cover 126 can be made of a softer polymer such as polyurethane or silicone.

Proximal opening 124 as defined by base 122 is configured to receive elongate member 12. In some examples, proximal opening 124 has a circular cross-section, but other cross-sectional shapes (e.g., quadrilateral, oval, etc.) are contemplated. In the example shown in FIG. 5A, proximal opening 124 has width 132 (e.g., width may be a diameter in the case of an opening with a circular cross-section). In addition, proximal opening 124 is sized to receive elongate member 12. For example, width 132 may be greater than a greatest dimension of elongate member 12 in a direction that is substantially perpendicular to a longitudinal axis of elongate member 12. For example, in FIG. 5A, width 132 of proximal opening 124 is sized to be larger than a diameter 134 of elongate member 12 in examples in which elongate member 12 has a circular cross-section. In one example, width 132 of proximal opening 124 is about 14 mm and diameter 134 of elongate member 12 is about 1.3 mm. In other examples, where medical system 10 is configured to insert two elongate members 12 through burr hole 16 using burr cap assembly 120, proximal opening 124 may be configured for both elongate members 12. Other dimensions are contemplated.

Burr cap assembly 120 is configured to be inserted at least partially in burr hole 16 and may help protect edges of burr hole 16. For example, base 122 may include or may be attached to shaft element 136 that wraps around the inside of and protects inside of burr hole 16. Shaft element 136 may be a substantially hollow cylinder. Shaft element 136 may be substantially circular in cross-section. Shaft element 136 may be integrally formed with base 122, or may be physically separate from base 122 and mechanically coupled to base 122. Base 122 may have any suitable configuration. Base 122 and shaft element 136 may be made from any suitable biocompatible material, including metals such as stainless steel or titanium or other biocompatible alloys such as polymers (e.g., polyurethane, polysulfone, or nylon). There are numerous additional options available for materials, and those listed above should be considered only as examples of materials which might be used. The selection of suitable materials may depend upon the circumstances surrounding the particular application involved, the therapy to be provided to the patient, and other factors.

In some examples, shaft elements 136 may define distal opening 114. Distal opening 114 may be a different size than proximal opening 124. Distal opening 114 may be sized to enable desired shifting of elongate member 12 in response to brain shift. To enable desired shifting of elongate member 12 in response to brain shift, distal opening 114 of burr cap assembly 120 may be larger in cross-section than proximal opening 124 of burr cap assembly 120 (e.g., even as burr hole 16 has a constant diameter within cranium 18). For example, even where width 132 of proximal opening is about 14 mm, width 112 of distal opening 114 may be 20 mm to allow approximately 5 mm of shift in every radial direction (e.g., when shifting member 52 has a width of 10 mm). In this way, burr hole assembly 120 may be configured to enable elongate member 12 to shift a predetermined amount while maintaining a relatively small upper profile. Other dimensions for width 112 for other amounts of predetermined shift allowances are also possible.

In the example shown in FIG. 5A, base 122 may include flange feature 162 that extends radially out from shaft element 136. Flange feature 162 of base 122 is configured to engage with cranium 18 outside of burr hole 16 while shaft element 136 is configured to engage with cranium 18 within burr hole 16. The intersection between base 122 and shaft 136 may cover the edges of burr hole 16. The extension of flange feature 162 of base 122 in a generally radially outward direction from shaft element 136 may help to limit the depth of insertion of shaft element 136 into burr hole 16 and secure burr cap assembly 120 to an outer surface (i.e., the surface opposite the surface closest to brain 22) of cranium 18.

In some examples, base 122 and cap 126 may be configured to minimize vertical height of the structure above the outer surface of cranium 18, which may help manage, minimize, and control the reossification (bone growth) of the burr hole 16 post-surgically.

In the example shown in FIG. 5A, base 122 is configured such that elongate member 12 extends from a side of burr cap assembly 120, rather than from a top (e.g., the surface furthest from cranium 18) of burr cap assembly 120 when burr cap assembly 120 is placed at least partially in burr hole 16. In one example, base 122 may define one or more grooves, including groove 138, which is configured to receive elongate member 12. Elongate member 12 may be configured to extend from burr cap assembly 120 through groove 138. In some examples, base 122 defines a plurality of grooves similar to groove 138, which may enable a clinician to select the point around base 122 by which elongate member 12 enters and exits burr cap assembly 120. In some examples, groove 138 as defined by base 122 may extend radially straight out from burr hole 16 or groove 138 may curve or angle in any suitable manner to guide elongate member 12 in a direction or trajectory desired by clinician.

In other examples, burr cap assembly 120 is configured such that elongate member 12 exits burr cap assembly 120 from another surface of assembly 120, such as from a top of burr cap assembly 120. For example, cover 126 may define an opening (not depicted) that substantially aligns with proximal opening 124 in base 122 when cover 126 is connected to base 122, and elongate member 12 may exit burr cap assembly 120 through the opening defined by cover 126. In some examples, this may permit the radius of curvature of elongate member 12 as it exits burr cap assembly 120 to be controlled, which may help maintain the integrity of elongate member 12. Other techniques for guiding elongate member 12 out of burr cap assembly 120 may be used. The techniques may be configured to guide elongate member 12 in a manner that helps maintain the mechanical integrity of elongate member 12.

Base 122 may be affixed to cranium 18 of patient 14 using any suitable technique, such as by suturing to the scalp or cranium 18 or via set screws. For example, base 122 may define apertures configured to receive one or more sutures, set screws, by mechanical interference fit, or by screwing base 122 into the burr hole itself. In some examples, at least a portion of base 122 may be formed from a compressible material, such that shaft element 136 of burr cap assembly 120 may be sized as needed to accommodate a predetermined range of sizes of burr hole 16. In other examples, base 122 is sized specifically for one size of burr hole 16.

Cover 126 is configured to be mechanically connected to base 122 and substantially cover (e.g., plug) opening 124 defined by base 122. In this way, cover 126 may substantially cover burr hole 16. In the example shown in FIG. 5A, cover 126 is configured to cover groove 138 (as well as any other grooves), such that when cover 126 is mechanically connected to base 122, elongate member 12 extends from burr cap assembly 120 through a relatively small opening defined between base 122 and cover 126. In some examples, burr cap assembly 120 may be configured to fix elongate member 12 substantially in place as elongate member 12 enters burr cap assembly 120, thereby substantially retaining the relative position between elongate member 12 (e.g., proximal portion 34 of elongate member 12) and burr hole 16 when burr cap assembly 20 is substantially fixed to cranium 18. Elongate member 12 may be fixed substantially in place by base 122, or both base 122 and cover 126. In other examples, burr cap assembly 120 may be configured to slidably receive elongate member 12 such that elongate member 12 may axially slide within groove 138 when cover 126 is mechanically connected to base 122 (e.g., axially slide in response to brain-shift).

In the example shown in FIG. 5A, elongate member 12 extends from proximal opening 124 defined by base 122 to distal opening 114 defined by shaft element 136 of burr cap assembly 120 to access a brain 22 of patient 14, which is positioned on the other side of cranium 18 from burr hole cover 126. When cover 126 is installed over base 122 and cover 126 is secured to base 122 (e.g., via a snap fit, an adhesive or any other suitable mechanically fixation), cover 126 may help retain the position of elongate member 12 relative to burr hole 16. This may help secure a portion of elongate member 12 as elongate member 12 enters burr cap assembly 120.

Elongate member 12 may be introduced into patient 14 using any suitable technique. In some examples, a distal section 24 of elongate member 12 may be guided to a target site 50 within patient 14 (e.g., within brain 22 of patient 14) with the aid of a stereotactic instrument, which may permit a very precise movement of shifting member 52 within patient 14. In some of these examples, cover 126 is configured to fit over base 122 while elongate member 12 is still retained by the stereotactic instrument and held in place relative to the target site 50 via the stereotactic instrument. Upon installation of cover 126 over base 122, cover 126 may substantially fix elongate member 12 in place relative to burr hole 16 at a point of entry into burr cap assembly 120.

In other examples, cover 126 may be configured to fit over base 122 after elongate member 12 is released from the stereotactic instrument. For example, base 122 may include one or more features that substantially fixes the position of elongate member 12 relative to base 122 prior to installation of cover 126. As an example, groove 138 may be configured to hold a portion of elongate member 12 retained in groove 138 by friction fit. The clinician implanting elongate member 12 in patient 14 may introduce elongate member 12 into groove 138 before or after release of elongate member 12 from the stereotactic instrument (or other instrument used to implant elongate member 12). Other techniques may also be used to substantially fix the position of elongate member 12 (e.g., proximal portion 34 of elongate member 12) relative to base 122 prior to installation of cover 126.

In the example shown in FIG. 5A, burr cap assembly 120 includes cavity 160. Cavity 160 may be substantially similar to cavity 60 as described above, with the exceptions of any differences described herein. As depicted in FIG. 5A, cavity 160 is defined by base 122 of burr cap assembly 120 as a substantially planar channel. Base 122 may define cavity 160 with a circular cross-section, substantially similar to the cross-section of proximal opening 124. Cavity 160 may be a substantially cylindrical cavity.

Cavity 160 may be defined by walls of burr cap assembly 120, such as by base 122 of burr cap assembly 120. For example, as depicted in the conceptual cross-sectional detail view 116 illustrated in FIG. 5B, cavity 160 is defined by lower wall 140 that is near cranium 18 and substantially tangential to cranium 18, upper wall 142 that is further from cranium 18 than lower wall 140 and substantially tangential to cranium, and side wall 144 that extends between lower wall 140 and upper wall 142 and is relatively perpendicular to cranium 18. Lower wall 140, upper wall 142, and side wall 144 may all be part of base 122. In some examples, side wall 144 may be substantially equivalent to wall 66 of FIGS. 2A-4B (e.g., such that structure 74 is base 122). In some examples, upper wall 142 and lower wall 144 may be treated or coated to be relatively lubricious. The lubricious coating may include high density polyethylene (HDPE), polytetrafluoroethylene (PTFE), a hydrophilic material, or the like. Treating upper wall 142 and/or lower wall 144 to be relatively lubricious may provide benefits in enabling elongate member 12 to shift in response to brain shift. Configuring base 122 to define cavity 160 may increase the ease of inserting elongate member 12 into burr cap assembly 120 that is configured to shift elongate member 12 in response to brain shift.

Burr cap assembly 120 further includes shifting member 152. Shifting member 152 may be substantially similar to shifting member 152 as described above, with the exceptions of any differences described herein. Shifting member 152 may be substantially cylindrical with a circular cross-section. For example, shifting member 152 may be a substantially circular plate. Shifting member 152 may be configured to retain elongate member 12. For example, shifting member 152 may be configured to eliminate/substantially restrict relative movement between shifting member 152 and adjacent portion 76 of distal section 24 of elongate member 12.

Shifting member 152 may define lower wall 146 such that lower wall 146 is configured to interface with lower wall 144 of cavity 160. Further, shifting member 152 may define upper wall 148 such that upper wall 148 is configured to interface with upper wall 142 of cavity 160. Further, shifting member 152 may define outer wall 150 such that outer wall 150 is configured to interface with side wall 144 of cavity 160. Lower wall 146 and upper wall 148 of shifting member 152 may be coated or treated to be lubricious as described herein. In some examples, lower wall 146 of shifting member 152 may be configured to create at least a partial seal with lower wall 140 of cavity 160, or upper wall 148 of shifting member may be configured to create at least a partial seal with upper wall 142 of cavity, or both. A seal may be created by including a layer of a relatively softer material (e.g., polyurethane or silicone) at the interfacing locations and/or configuring interfacing walls 146, 140 or 148, 142 to have an interference fit. In other examples, burr cap assembly 120 may create a seal through a jaw mechanism of shifting member 152 axially retaining elongate member 12 and the labyrinth-type seal enclosing shifting member 152 as depicted in FIG. 5A (e.g., with the body of patient 14 naturally creating any additional seal through fibrosis). Configuring burr cap assembly 120 to establish a seal between some portion of shifting member 152 and walls 142, 140 of cavity 160 may increase the ability of burr cap assembly 120 to maintain a desired pressure gradient between brain 22 and air external to cranium 18.

In some examples, burr cap assembly 120 may be manufactured and packaged with shifting member 152 sealed within cavity 160 (e.g., shifting member 152 physically located within cavity 160), such that it is difficult or impossible to remove shifting member 152 from cavity 160 without damaging either shifting member 152 or walls 140, 142, 144 of cavity 160. In other examples, shifting member 152 may be located within cavity 160 during a process of assembling burr cap assembly 120. For example, a second member (e.g., a retention member as discussed below) that defines walls 140, 142, 144 of cavity 160 may be removeable from base 122 and may "hinge" open (e.g., hinge open along plane 54 of shifting member 152) to receive shifting member 152, after which the second member may be located and/or attached within base 122 as depicted. For another example, a clinician may attach a component defining lower wall 144 to base 122 within proximal opening 124, after which the clinician may place shifting member 152 within proximal opening 124 on top of lower wall 144, after which the clinician may attach a component defining upper wall 148 to base 122 to create cavity 160. The components defining lower wall 144 and upper wall 142 may be attached to base 122 using any suitable technique, such as by using a glue, using a mechanical attachment mechanism (e.g., mating features between base 122 and the components), or by a slot of base 122 that creates an interference fit with the components defining lower wall 144 and upper wall 142.

Figure 6:
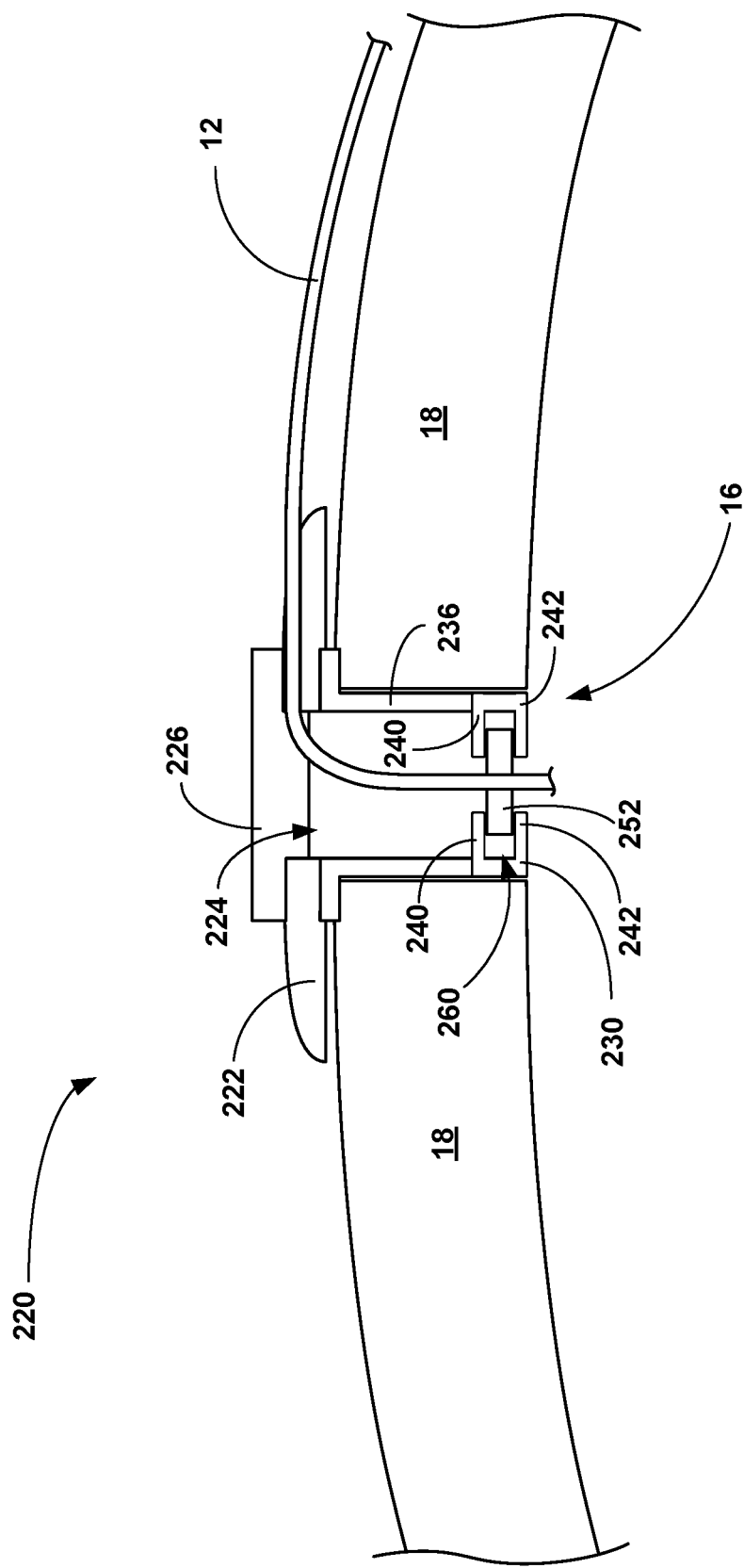
FIG. 6 is a conceptual cross-sectional side view of an example burr cap assembly in a burr hole with a retention member that houses the shifting member and is attached to an example shaft of the burr cap assembly that is at least partially within the burr hole, in accordance with an example of this disclosure.

In some examples, an example shifting member may move within an example cavity that is defined by a separate component of the burr cap assembly 120 (e.g., rather than the base 122 of the burr cap assembly 120). For example, FIG. 6 is a conceptual diagram illustrating burr cap assembly 220 that includes base 222, cap 226, shaft element 236, shifting member 252, and a retention member 230. Shifting member 252 is a first member that is retained within cavity 260 defined by a second member, i.e., retention member 230. Burr cap assembly 220 may be substantially similar to burr cap assemblies as described above, with the exception of any differences described herein. Burr cap assembly 220 may include at least base 222, cover 226, shaft element 236, a first member that is configured to radially retain elongate member 12 while shifting in response to brain shift (e.g., shifting member 252), and a second member (e.g., retention member 230) that defines cavity 260. In other examples, shifting member 252 may be a separate component to burr cap assembly 220, configured to move relative to a substantially stationary burr cap assembly 220.

Retention member 230 may be connected to shaft element 236. For example, second member 230 may be bonded (e.g., welded, glued) or mechanically attached (e.g., through one or more mating components) to shaft element 236). As discussed above, shaft element 236 may be connected to base 222 or shaft element 236 may be integrally formed with base 222 as a unitary structure. Second member 230 may be made of any of the biocompatible metals or more rigid polymers described herein.

As defined by second, retention member 230, cavity 260 may be a substantially cylindrical planar channel in which shifting member 252 moves. The planar channel may be defined by a top portion 240 and a bottom portion 242. Second member 230 may be closer to brain 22 than shaft element 236. In some examples, top portion 240 of retention member 230 may be attached to shaft element 236 such that retention member 230 is at least partially within brain 22. Positioning retention member 230 such that retention member 230 is close to or at least partially within brain 22 may improve an ability of shifting member 252 and adjacent portion 76 of distal section 24 of elongate member 12 to shift with brain 22. Positioning retention member 230 close to brain 22 may improve this ability as forces (e.g., force 80 from FIG. 3 or force 90 from FIG. 4) may have less axial distance to travel before they are addressed/negated (e.g., by shifting member 252 and elongate member 12 moving) when retention member 230 is closer to brain 22 and therein closer to the forces. By positioning retention member 230 closer to the forces, medical system 10 potentially reduces or eliminates an ability of these forces to partially migrate electrodes 26 from target site 50 before shifting member 252 and elongate member 12 shift to address/negate these forces.

Figure 7:
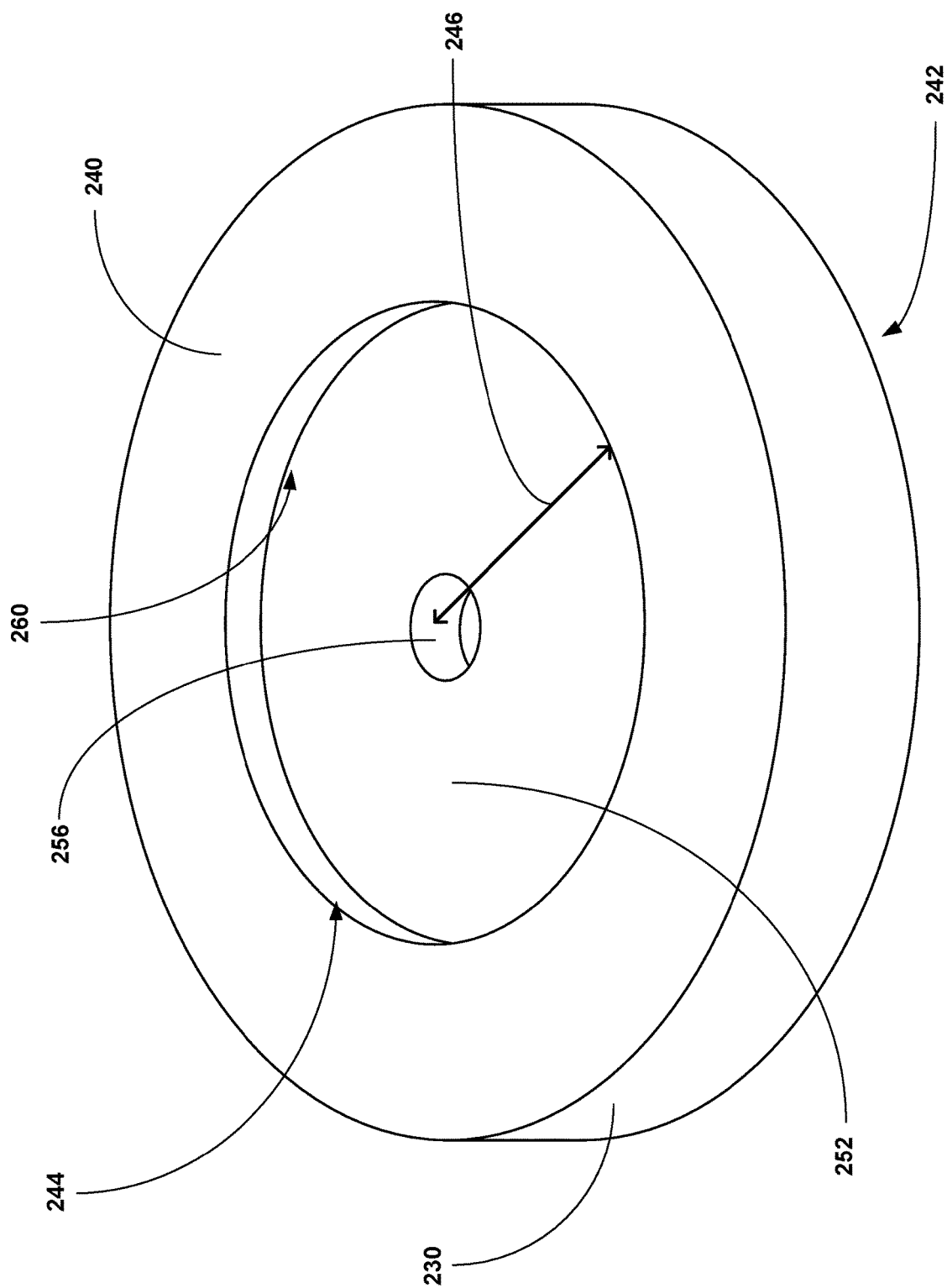
FIG. 7 is a conceptual perspective illustration of the retention member and shifting member of FIG. 6, in accordance with an example of this disclosure.

In some examples, as described above, retention member 230 may be an independent separate component before it is connected to shaft element 236. For examples, FIG. 7 is a conceptual perspective illustration of retention member 230 and shifting member 252. As depicted in FIG. 7, retention member 230 defines a substantially circular cross section. Retention member 230 may be substantially hollow to define cavity 260. Shifting member 252 is within cavity 260. As discussed above, shifting member 252 may be manufactured and shipped to clinician inside cavity 260 of retention member 230, or shifting member 252 may be assembled inside retention member 230 by clinician using a "sandwich" assembling process or through a hinged mechanism of retention member 230 that exposes cavity 260 of retention member 230. In some examples, once shifting member 252 is within cavity 260 of retention member 230 it may be difficult or impossible to remove shifting member 252 from cavity 260 of retention member 230 without destroying or otherwise damaging or disassembling either shifting member 252 or retention member 230.

As discussed herein, shifting member 252 includes hole 256 to receive elongate member 12. In some examples, top portion 240 and bottom portion 242 may be configured to not obscure hole 256 even when the outer wall of shifting member 252 (e.g., wall 150 of shifting member 152) contacts the side wall of cavity 260 (e.g., wall 144 of cavity 160). Further, in some examples, top portion 240 and bottom portion 242 may define openings 244 with a radius 246 small enough such that an outer wall of shifting member 252 may not be exposed through opening 244, even if the opposite outer wall of shifting member 252 contacts the side wall of cavity 260.

Figure 8:
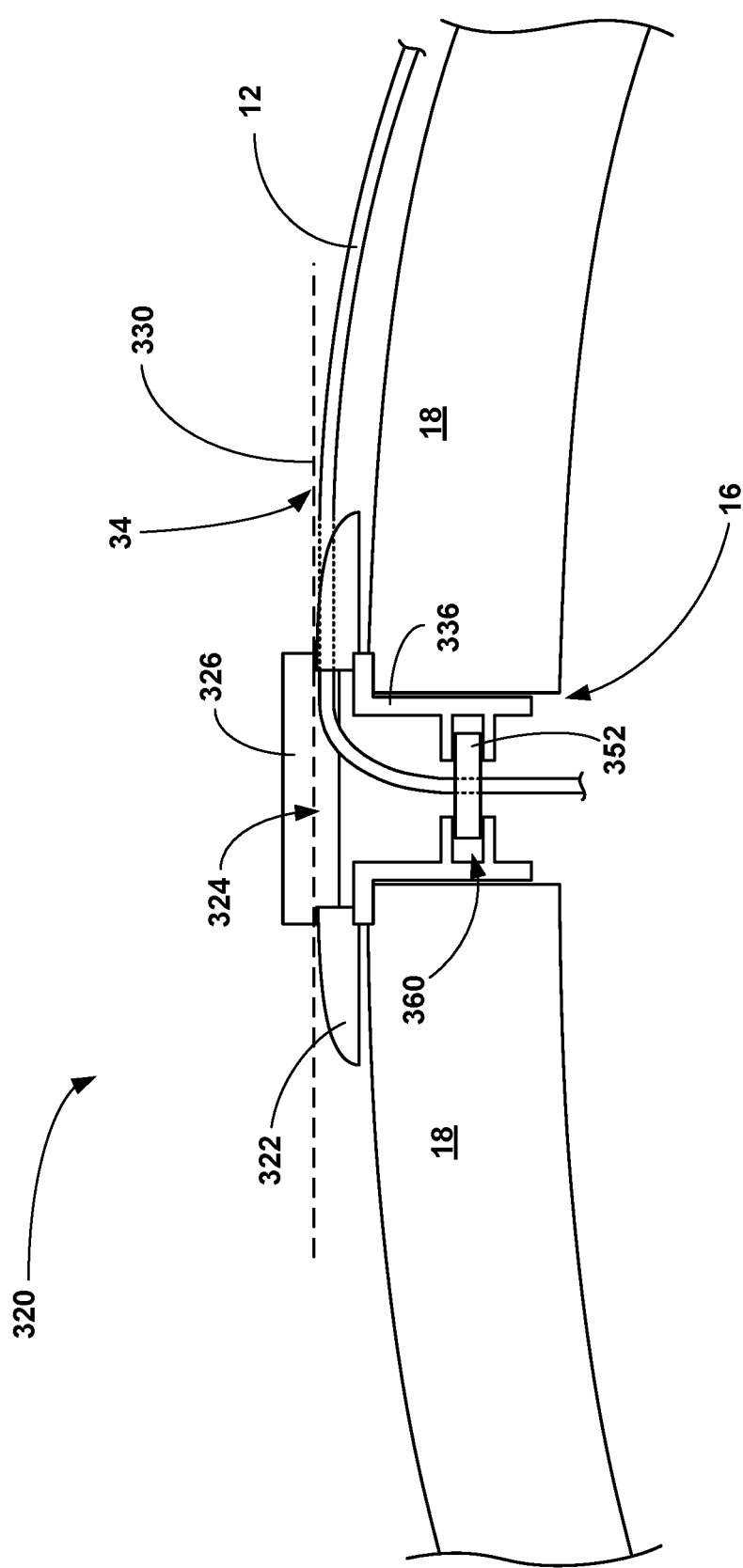
FIG. 8 is a conceptual cross-sectional side view of an example burr cap assembly in a burr hole with an example shifting member in an example shaft of the burr cap assembly that is at least partially within the burr hole, in accordance with an example of this disclosure.

In some examples, an example cavity is not defined by either retention member 230 or base 122, but instead by a shaft element. For example, FIG. 8 is a conceptual diagram illustrating burr cap assembly 320 that includes base 322, cap 324, shaft element 336, and shifting member 352 in cavity 360. Burr cap assembly 320 may be substantially similar to burr cap assemblies as described above, with the exception of any differences described herein. Burr cap assembly 320 may include at least base 322, cover 326, shaft element 336, first member 352 that shifts while retaining elongate member 12 (e.g., shifting member 352), and cavity 360. In some examples, burr cap assembly 320 includes a second member that defines cavity 360 (e.g., a retention member). In other examples, shifting member 352 may be a separate component to burr cap assembly 320, configured to move relative to a substantially stationary burr cap assembly 320. Shaft element 336 may define cavity 360. Shaft element 336 may define cavity 360 to be substantially cylindrical. Shaft element 336 may define cavity 360 anywhere within burr hole 16. As discussed above, shaft element 236 may be connected to base 322 or shaft element 236 may be unitary with base 322.

As defined by shaft element 336, cavity 360 may be a planar channel in which shifting member 352 moves. Shaft element 336 may define cavity 360 relatively closer to brain 22 in comparison to where base 322 may be capable of defining a cavity (e.g., as base 122 defines cavity 160 in FIG. 5A). Positioning cavity 360 closer to brain 22 may improve an ability of shifting member 352 and elongate member 12 to shift with brain 22. Positioning cavity 360 closer to brain 22 may improve this ability by functionally reducing a length of the lever arm between where the force is applied to elongate member 12 by fluids of brain and where force is addressed negated through shifting member 352. as forces may have less axial distance to travel before they are addressed/negated. By positioning cavity 360 closer to the forces, medical system 10 potentially reduces or eliminates an ability of these forces to partially migrate electrodes 26 from target site 50 before shifting member 352 and elongate member 12 shift to address/negate these forces.

Similar to burr cap assemblies 120, 220 described above, shifting member 352 may be manufactured and packaged with shifting member 352 sealed within cavity 360, or a clinician may assemble shifting member 352 within cavity 360. For example, similar to the discussion above, a second member (e.g., a retention member as discussed above) that defines a set of walls (e.g., similar to walls 140, 142, 144) of cavity 360 may be removeable from shaft element 336 and may "hinge" open (e.g., hinge open along plane 54 of shifting member 352) to receive shifting member 352, after which the second member may be located and/or attached within shaft element 336 as depicted. For another example, similar to the discussion above, a clinician may attach two or more separate components defining two or more portions of a lower wall of cavity 360 (e.g., similar to lower wall 144) to shaft element 336 within proximal opening 324, after which the clinician may place shifting member 352 within proximal opening 324 on top of the lower wall of cavity 360, after which the clinician may attach two or more components defining two or more portions of an upper wall of cavity 360 (e.g., similar to upper wall 148) to shaft element 336 to create cavity 360. The components defining the walls of cavity 360 may be attached to shaft element 336 using any suitable technique, such as the techniques described herein. After shifting member 352 is within cavity 360, a clinician may place cover 326 on base 322 (e.g., along plane 330) to seal burr cap assembly 320 and secure proximal portion 34 of elongate member 12.

Figure 9:
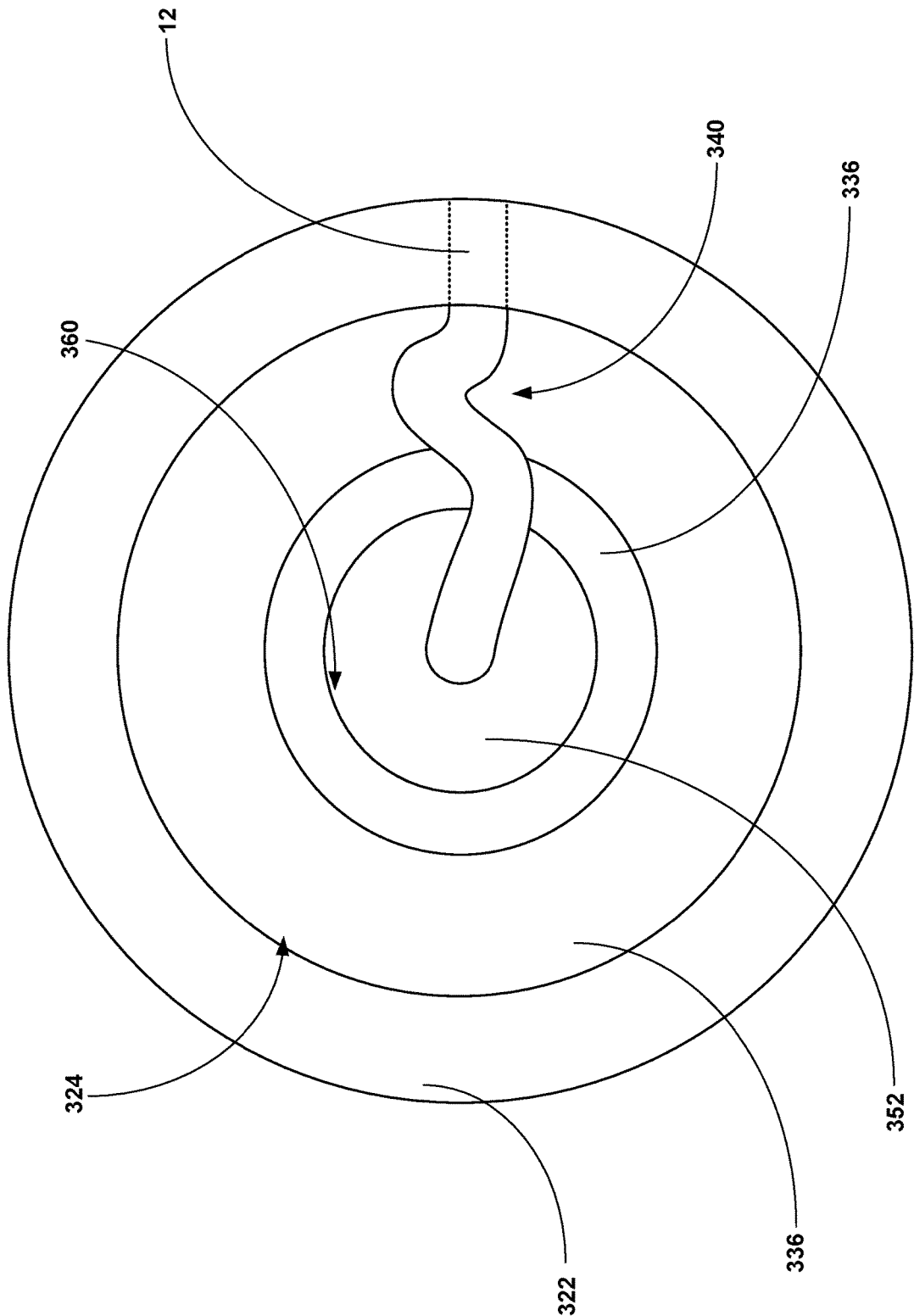
FIG. 9 is a conceptual cross-sectional plan illustration of the burr cap assembly of FIG. 8, in accordance with an example of this disclosure.

In some examples, burr cap assemblies 320 may include a slack portion of elongate member 12 to enable elongate member 12 shifting in response to brain shift. For example, FIG. 9 is a conceptual top-down cross-sectional illustration of the burr cap assembly of FIG. 8 as viewed from plane 330. As depicted in FIG. 9, elongate member 12 includes a slack portion 340. Slack portion 340 of elongate member 12 may be a portion of the elongate member 12 that is not taut, but is instead coiled or slack within proximal opening 324, such that slack portion 340 is configured to enable some or all of distal section 24 of elongate member 12 to shift without moving or applying a substantial axial force upon proximal portion 34 of elongate member 12. Slack portion 340 may be within proximal opening 324, such that elongate member 12 may shift within burr cap assembly 320 without moving proximal portion 34 of elongate member 12. Slack portion 340 may be sufficient to allow elongate member 12 that is within proximal opening 324 to move with shifting member 352 without moving proximal portion 34 of elongate member 12.

Figure 10:
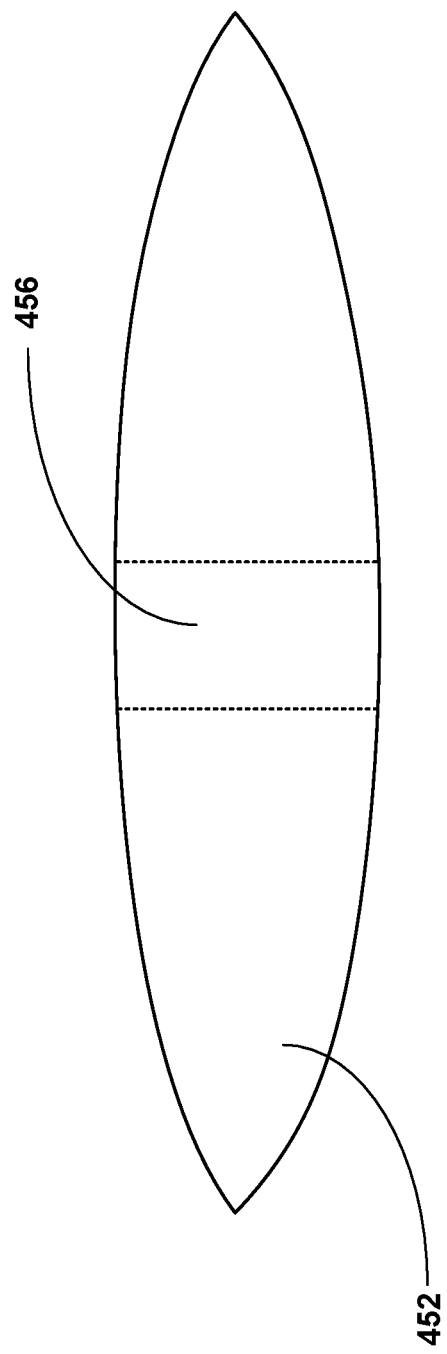
FIG. 10 is a conceptual cross-sectional side view of an example shifting member of an example burr cap assembly, in accordance with an example of this disclosure.

In some examples, rather than being circular disk- or plate-shaped (e.g., as in FIG. 2B), shifting members 52, 152, 252, or 352 of FIGS. 2A-4B, 5A and 5B, 6 and 7, or 8 and 9 respectively, may be convex-shaped. For example, FIG. 10 is a conceptual side view illustration of shifting member 452 that is generally convex-shaped. Shifting member 452 includes a hole 456 through which elongate member 12 may be inserted. In some examples, configuring shifting member 452 to define a convex shape may improve the ability of shifting member 452 to move radially within a respective cavity. In some example, this respective cavity may be reshaped for the convex shape, such as with a reduced height around the outer wall (e.g., outer wall 66) of the respective cavity.

Figure 11:
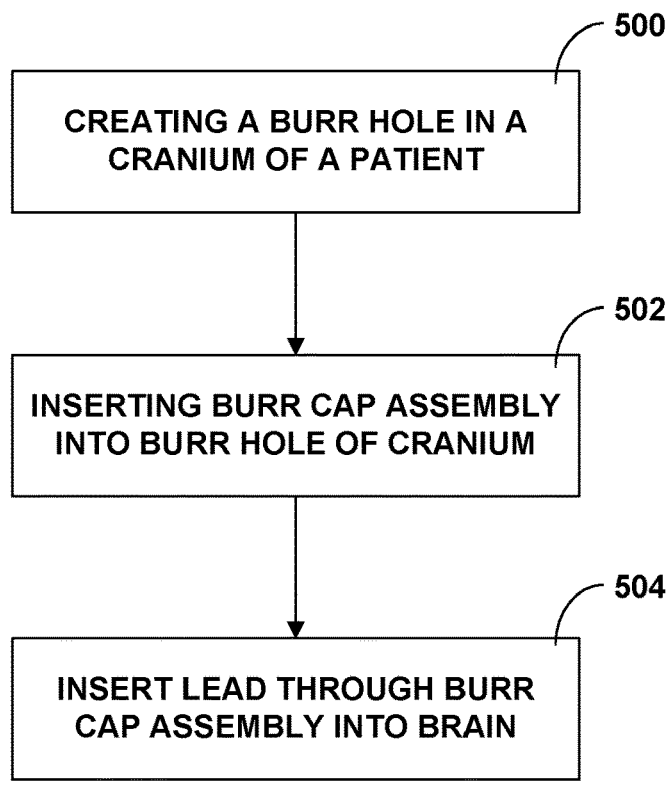
FIG. 11 is an example method of a clinician inserting an example burr cap assembly at least partially within a burr hole, in accordance with an example of this disclosure.

A clinician may insert a burr cap assembly within a burr hole in the cranium of a patient. FIG. 11 depicts an example method of inserting a burr cap assembly for use within a patient. Although FIG. 11 is discussed primarily in the context of the burr cap assembly 20 of FIGS. 1 and 2A, it is to be understood that other examples of burr cap assemblies as described herein are also applicable to the method of FIG. 11.

A clinician may create burr hole 16 in cranium 18 of patient 14 (500). The clinician may create burr hole 16 using any suitable technique, such as drilling or cutting cranium 18 to create burr hole 16. Burr hole 16 may be positioned to be relatively close to target site 50 within brain 22 of patient 14. The clinician may create burr hole 16 to define a size/diameter to receive burr cap assembly 20. For example, the clinician may create burr hole 16 to define a diameter that is essentially the same size as or nominally bigger than an outer diameter of a portion of burr cap assembly 20 that is at least partially inserted into burr hole 16 (e.g., the partially inserted portion of burr cap assembly 20 being similar to one of shaft element 136 of FIG. 5A).

The clinician may create burr hole 16 based on a desired distance that shifting member 52 and elongate member 12 may move in response to brain shift as defined by cavity 60. In some examples, the clinician may create burr hole 16 to partially define space 62 (e.g., in conjunction with cavity 60), as elongate member 12 may only be able to radially move in a dimension a distance less than the diameter of burr hole 16. For example, if the clinician selects cavity 60 with a 16 mm diameter, the clinician may create burr hole 16 with a 20 mm diameter (e.g., to provide room for shaft element 126, 226, 326), whereas if the clinician selects cavity 60 with a 10 mm diameter, the clinician may create burr hole 16 with a 14 mm diameter.

The clinician may insert burr cap assembly 20 into burr hole 16 of cranium 18 of patient 14 (502). Burr cap assembly 20 may be inserted partially into burr hole 16, such that only a portion of burr cap assembly 20 is within burr hole 16. Burr cap assembly 20 may be configured such that burr cap assembly 20 distally terminates before extending past cranium 18 (e.g., by configuring shaft elements 136 to only extend partway into cranium 18). In other examples, burr cap assembly 20 may extend through burr hole 16, such that some portion of burr cap assembly 20 is within a portion of cranium 18 (e.g., and therein contacting brain 22) as a result of extending through burr hole 16.

Burr cap assembly 20 may be configured to protect burr hole 16 while extending through burr hole 16. For example, burr cap assembly 20 may encapsulate and cover an exposed edge of burr hole 16 to avoid damaging burr hole 16 and to reduce the chances of other objects contacting and damaging burr hole 16. The clinician may securely fasten burr cap assembly 20 to burr hole 16 once burr cap assembly 20 is correctly positioned within burr hole 16. Clinician may fasten burr cap assembly 20 to burr hole 16 using any number of means, such as, for example, screwing or suturing burr cap assembly 20 to cranium 18 of patient 14.

The clinician may insert elongate member 12 through burr cap assembly 20 (504). The clinician may insert elongate member 12 through shifting member 52 that is within cavity 60 of burr cap assembly 20. For example, the clinician may guide elongate member 12 through hole 56 that is generally in the center of shifting member 52. Once elongate member 12 is within hole 56 of shifting member 52, shifting member 52 may substantially radially retain elongate member 12 (e.g., retain elongate member 12 in dimensions that are radial to elongate member 12), such that elongate member 12 may not move radially within burr cap assembly 20 unless shifting member 52 moves radially within burr cap assembly 20.

In some examples, elongate member 12 may extend through shifting member 52 in such a way that shifting member 52 creates a seal around elongate member 12 to maintain a proper pressure gradient within brain 22 of patient 14. In other examples, burr cap assembly 20 may radially and axially retain elongate member 12 with a jaw mechanism as described herein, enabling body of patient 14 to naturally create a seal post-operatively via fibrosis.

Elongate member 12 may extend through burr cap assembly 20 out a distal opening of burr cap assembly 20 to be implanted at least partially within brain 22. For example, only a distal section 24 of elongate member 12 may be implanted in brain 22 through burr cap assembly 20. The clinician may insert elongate member 12 through burr cap assembly 20 once burr cap assembly has been inserted into and securely fastened to cranium 18. In some examples, elongate member 12 may be guided through burr cap assembly 20 prior to burr cap assembly 20 being inserted into and/or securely fastened to cranium 18 of patient 14. In some examples, after burr cap assembly 20 is inserted into and secured to cranium 18 and elongate member 12 is inserted through burr cap assembly 20, burr cap assembly 20 may be sealed, such as sealed with a cover (e.g., cover 126, cover 226, or cover 326). Sealing burr cap assembly 20 may maintain a proper pressure gradient within brain 22 of patient 14.

A clinician may subcutaneously insert proximal portion 34 of elongate member 12 into patient 14. The clinician may further implant IMD 28 within patient 14. The clinician may implant IMD 28 anywhere within the body of patient 14, such as near the shoulder or side of patient 14. The clinician may insert proximal portion 34 of elongate member 12 subcutaneously to the location of IMD 28 to couple proximal end 30 of elongate member 12 to IMD 28.

Figure 12:
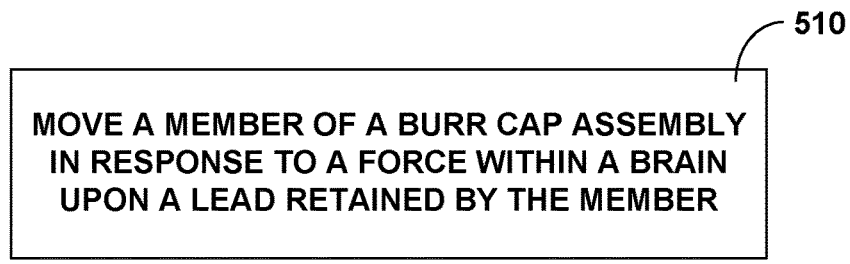
FIG. 12 is an example method of operation of an example burr cap assembly in permitting elongate member shift in response to brain shift, in accordance with an example of this disclosure.

Once medical system 10 is fully inserted within patient 14, components of burr cap assembly 20 may actuate in response to forces of brain 22. For example, FIG. 12 depicts an example method of burr cap assembly 20 actuating in response to brain shift. Though FIG. 12 is discussed primarily in the context of the burr cap assembly 20 of FIGS. 1 and 2A, it is to be understood that other examples of burr cap assemblies as described herein are also applicable to the method of FIG. 12. As discussed above, a clinician may have inserted burr cap assembly 20 at least partially within burr hole 16 and inserted elongate member 12 through burr cap assembly 20 into brain 22 of patient 14.

Upon insertion or implantation of burr cap assembly 20, shifting member 52 of burr cap assembly 20 may move in response to brain shift (510). For example, shifting member 52 may move in response to a force (e.g., force 80 of FIG. 3A or force 90 of FIG. 4A as a result of brain shift) upon distal section 24 of elongate member 12 within brain 22. Shifting member 52 may move in one or more directions in a plane within cavity 60 of burr cap assembly 20. Being as shifting member 52 radially retains elongate member 12, elongate member 12 may radially move with shifting member 52 in response to the force. In this way, an adjacent portion 76 of distal section 24 of elongate member 12 that is immediately distal to burr cap assembly 20 may effectively migrate with brain 22 during recovery from brain shift to improve an ability of electrodes 26 at more distal portion 78 of distal section 24 of elongate member 12 to stay within target site 50 and reduce a possibility of distal components 26 of elongate member 12 migrating away from target area 50 (e.g., as a result of electrodes migrating axially back towards burr hole 16).

Shifting member 52 may move in the one dimension substantially along plane 54 that is substantially perpendicular to longitudinal axis 58 of distal section 24 of elongate member 12. In some examples, after shifting member 52 moves in one dimension of plane 54, shifting member 52 may move in a second, different dimension of plane 54. As an illustration, brain shift may initially move towards a front of cranium 18 (e.g., towards patient's 14 face) before shifting 90° radially towards a side of cranium 18 (e.g., towards patient's 14 ear). In this example, shifting member 52 (and adjacent portion 76 of distal section 24 of elongate member 12) would move in a first dimension towards the front of cranium 18 after which shifting member 52 would move in a second dimension towards the side of cranium 18. In other examples, shifting member 52 may move in more dimensions, or shifting member 52 may be constrained within cavity 60 such that shifting member 52 may only move in a predetermined number of dimensions (e.g., one dimension).

Various examples have been described. These and other examples are within the scope of the following claims.

What is claimed is:

1. An implantable medical device comprising:
a burr cap assembly configured to be positioned at least partially within a burr hole in a cranium of a patient, the burr cap assembly defining a cavity and being configured to enable implantation of at least a portion of an implantable medical elongate member into a brain of the patient through the burr cap assembly, the burr cap assembly including a member positioned within the cavity of the burr cap and defining at least one opening to enable passage of at least a portion of the implantable medical elongate member into the brain of the patient, the member of the burr cap assembly being configured to, while the implantable medical elongate member is secured by the burr cap assembly, move within the cavity relative to the burr cap within at least one dimension of a plane that is substantially perpendicular to a longitudinal axis of at least a portion of the implantable medical elongate member.

2. The implantable medical device of claim 1, wherein the member of the burr cap assembly is a first member, the burr cap assembly comprising a second member that defines the cavity, wherein the second member of the burr cap assembly is configured to be positioned at least partially within the cranium of the patient when the burr cap assembly is positioned at least partially within the burr hole.

3. The implantable medical device of claim 1, wherein the member of the burr cap assembly is a first member, the burr cap assembly comprising a second member that defines the cavity, wherein the second member of the burr cap assembly is configured to be positioned at least partially above the cranium of the patient when the burr cap assembly is positioned at least partially within the burr hole.

4. The implantable medical device of claim 1, wherein the member of the burr cap assembly is a first member, the burr cap assembly comprising a second member that defines the cavity, wherein the second member of the burr cap assembly includes a top portion and a bottom portion that define a planar channel for movement of the first member of the burr cap assembly within the cavity.

5. The implantable medical device of claim 1, wherein the member of the burr cap assembly is configured to move within the cavity in response to a first force applied to the member of the burr cap assembly by the implantable medical elongate member following implantation of the at least a portion of the implantable medical elongate member in the brain of the patient.

6. The implantable medical device of claim 5, wherein the first force is applied to the member of the burr cap assembly in response to a second force applied to the implantable medical elongate member by fluids of the brain of the patient following implantation of the at least a portion of the implantable medical elongate member in the brain of the patient.

7. The implantable medical device of claim 1, wherein the member of the burr cap assembly includes a substantially circular plate.

8. The implantable medical device of claim 1, wherein the burr cap assembly defines the cavity to substantially restrict movement of the member of the burr cap assembly in a direction substantially parallel to the longitudinal axis of at least a portion of the implantable medical elongate member.

9. The implantable medical device of claim 1, wherein the opening is configured to substantially restrict relative movement between the member of the burr cap assembly and a portion of the implantable medical elongate member extending through the opening defined by the member of the burr cap assembly in a direction substantially perpendicular to the longitudinal axis of the at least a portion of the implantable medical elongate member.

10. The implantable medical device of claim 1, wherein the burr cap assembly is sized to receive a slack portion of the implantable medical elongate member.

11. The implantable medical device of claim 2, wherein the cavity is substantially cylindrical.

12. The implantable medical device of claim 1, wherein the member of the burr cap assembly is configured to move within the cavity relative to the burr cap assembly within two dimensions of the plane.

13. A method comprising:
inserting a portion of an implantable medical elongate member through an opening of a member of a burr cap assembly configured to be positioned at least partially within a burr hole in a cranium of a patient such that at least a portion of the implanted medical elongate member extends into a brain of the patient, wherein the member of the burr cap assembly is configured to be positioned within a cavity defined by the burr cap assembly and configured to, while the implantable medical elongate member is secured by the burr cap assembly, move within the cavity and in at least one dimension of a plane that is substantially perpendicular to a longitudinal axis of the at least the portion of the implantable medical elongate member, the member of the burr cap assembly being configured to enable movement of the at least a portion of the implantable medical elongate member in response to a force applied to the member of the burr cap assembly by the implantable medical elongate member following implantation of the at least the portion of the implantable medical elongate member in the brain of the patient.

14. The method of claim 13, wherein the at least one dimension is a first dimension, wherein the member of the burr cap assembly is configured to move within the cavity relative to the burr cap assembly in both the first dimension and a second dimension along the plane that is substantially perpendicular to the longitudinal axis of at least the portion of the implantable medical elongate member.

15. The method of claim 13, wherein the member of the burr cap assembly is configured to move in the second dimension after moving in the first dimension, the member of the burr cap assembly being configured to move in the second dimension in response to a new force applied to the member of the burr cap assembly by the implantable medical elongate member following implantation of the at least a portion of the implantable medical elongate member in the brain of the patient.

16. The method of claim 13, wherein the member of the burr cap assembly is configured to move in the at least one dimension until an outer wall of the member of the burr cap assembly contacts an inner wall of the cavity.

17. An implantable medical device comprising:
a burr cap assembly configured to be positioned at least partially within a burr hole in a cranium of a patient, the burr cap assembly defining a cavity, the burr cap assembly including a member positioned within the cavity of the burr cap assembly and defining at least one opening, the member of the burr cap assembly being configured to, while the implantable medical elongate member is secured by the burr cap assembly, move within the cavity relative to the burr cap assembly within at least one dimension of a plane that is substantially perpendicular to a longitudinal axis of at least a portion of the implantable medical elongate member; and
the implantable medical elongate member, wherein at least a portion of the implantable medical elongate member is configured to be implanted into a brain of the patient through both the burr cap assembly and the at least one opening defined by the member of the burr cap assembly, wherein the burr cap assembly comprises a cover configured to retain the implantable medical elongate member at a location in which the implantable medical elongate member enters the burr cap assembly, the cover configured to substantially seal the burr cap.

18. The implantable medical device of claim 17, wherein the member of the burr cap assembly is a first member, the burr cap assembly comprising a second member that defines the cavity, wherein the second member of the burr cap assembly is configured to be positioned at least partially within the cranium of the patient when the burr cap assembly is positioned at least partially within the burr hole.

19. The implantable medical device of claim 17, wherein the member of the burr cap assembly is a first member, the burr cap assembly comprising a second member that defines the cavity, wherein the second member of the burr cap assembly is configured to be positioned at least partially above the cranium of the patient when the burr cap assembly is positioned at least partially within the burr hole.

20. The implantable medical device of claim 17, wherein the member of the burr cap assembly is configured to move within the cavity in response to a first force applied to the member of the burr cap assembly by the implantable medical elongate member following implantation of the at least a portion of the implantable medical elongate member in the brain of the patient.

21. The implantable medical device of claim 20, wherein the first force is applied to the member of the burr cap assembly in response to a second force applied to the implantable medical elongate member by fluids of the brain of the patient following implantation of the at least a portion of the implantable medical elongate member in the brain of the patient.

22. The implantable medical device of claim 17, wherein the burr cap assembly defines the cavity to substantially restrict movement of the member of the burr cap assembly in a direction substantially parallel to the longitudinal axis of the at least a portion of the implantable medical elongate member.

23. The implantable medical device of claim 17, wherein the opening is configured to substantially restrict relative movement between the member of the burr cap assembly and a portion of the implantable medical elongate member extending through the opening defined by the member of the burr cap assembly in a direction substantially perpendicular to the longitudinal axis of the at least a portion of the implantable medical elongate member.

24. The implantable medical device of claim 17, wherein the burr cap assembly is sized to receive a slack portion of the implantable medical elongate member.

25. The implantable medical device of claim 17, wherein the member of the burr cap assembly is configured to move within the cavity relative to the burr cap assembly within two dimensions of the plane.

* * * * *